(12) United States Patent
Saal et al.

(10) Patent No.: US 8,277,437 B2
(45) Date of Patent: Oct. 2, 2012

(54) METHOD OF ACCESSING TWO LATERAL RECESSES

(75) Inventors: Jeffrey Alan Saal, Portola Valley, CA (US); Joel Stuart Saal, Portola Valley, CA (US); Brian Robert Dubois, Redwood City, CA (US); James T. Nielsen, San Francisco, CA (US)

(73) Assignee: Laurimed, LLC, Redwood City, CA (US)

( * ) Notice: Subject to any disclaimer, the term of this patent is extended or adjusted under 35 U.S.C. 154(b) by 588 days.

(21) Appl. No.: 12/417,165

(22) Filed: Apr. 2, 2009

(65) Prior Publication Data

US 2009/0259126 A1    Oct. 15, 2009

Related U.S. Application Data

(60) Provisional application No. 61/123,028, filed on Apr. 2, 2008.

(51) Int. Cl.
*A61M 31/00* (2006.01)
(52) U.S. Cl. ....................................... 604/508
(58) Field of Classification Search ................ 604/131, 604/506, 508, 512
See application file for complete search history.

(56) References Cited

U.S. PATENT DOCUMENTS

| | | |
|---|---|---|
| 1,527,291 A | 2/1925 | Zorraquin |
| 1,733,502 A | 10/1929 | Linsley |
| 2,895,455 A | 7/1959 | Clowes |
| 3,081,770 A | 3/1963 | Hunter |
| 3,469,580 A | 9/1969 | Huddy |
| 3,682,162 A | 8/1972 | Colyer |
| 3,689,955 A | 9/1972 | Winkelmann |
| 3,709,211 A | 1/1973 | Hawkins |
| 3,782,381 A | 1/1974 | Winnie |
| 3,815,604 A | 6/1974 | O'Malley et al. |
| 3,884,238 A | 5/1975 | O'Malley et al. |
| 3,941,127 A | 3/1976 | Froning |
| 3,943,932 A | 3/1976 | Woo |
| 3,977,400 A | 8/1976 | Moorehead |
| 4,013,080 A | 3/1977 | Froning |
| 4,068,659 A | 1/1978 | Moorehead |
| 4,192,319 A | 3/1980 | Hargens et al. |
| 4,314,560 A | 2/1982 | Helfgott et al. |
| RE30,966 E | 6/1982 | Hargens et al. |
| 4,349,023 A | 9/1982 | Gross |
| 4,368,730 A | 1/1983 | Sharrock |
| 4,507,167 A | 3/1985 | Jahme et al. |

(Continued)

FOREIGN PATENT DOCUMENTS

RU    2029533    2/1995

(Continued)

OTHER PUBLICATIONS

Sice et al. "Epidural analgesia after spinal surgery via intervertebral foramen," *Bristish Journal of Anaesthesia*, 94(3), pp. 378-380, Dec. 24, 2004.

*Primary Examiner* — Kevin C Sirmons
*Assistant Examiner* — Bradley Osinski
(74) *Attorney, Agent, or Firm* — Levine Bagade Han LLP

(57) ABSTRACT

Device and method are provided for diagnosing and treating diseases and injuries to the spine by injecting drugs into the diseased or injured area. The device and method of the subject invention provide improvements to patient and operator safety, along with ease-of-use and convenience improvements over conventional techniques.

16 Claims, 11 Drawing Sheets

U.S. PATENT DOCUMENTS

| | | |
|---|---|---|
| 4,511,356 A | 4/1985 | Froning et al. |
| 4,580,573 A | 4/1986 | Quinn |
| 4,588,399 A | 5/1986 | Nebergall et al. |
| 4,609,370 A | 9/1986 | Morrison |
| 4,662,869 A | 5/1987 | Wright |
| 4,678,459 A | 7/1987 | Onik et al. |
| 4,721,506 A | 1/1988 | Teves |
| 4,737,146 A | 4/1988 | Amaki et al. |
| 4,775,637 A | 10/1988 | Sutherland et al. |
| 4,808,157 A | 2/1989 | Coombs |
| 4,842,585 A | 6/1989 | Witt |
| 4,846,799 A | 7/1989 | Tanaka et al. |
| 4,886,067 A | 12/1989 | Palermo |
| 4,917,668 A | 4/1990 | Haindl |
| 4,917,670 A | 4/1990 | Hurley et al. |
| RE33,258 E | 7/1990 | Onik et al. |
| 4,940,458 A | 7/1990 | Cohn |
| 4,958,901 A | 9/1990 | Coombs |
| 4,973,305 A | 11/1990 | Goltzer |
| 4,973,312 A | 11/1990 | Andrew |
| 4,994,036 A | 2/1991 | Biscoping et al. |
| 5,004,456 A | 4/1991 | Botterbusch et al. |
| 5,007,902 A | 4/1991 | Witt |
| 5,024,655 A | 6/1991 | Freeman et al. |
| 5,026,350 A | 6/1991 | Tanaka et al. |
| 5,078,679 A | 1/1992 | Reese |
| 5,085,631 A | 2/1992 | Leighton |
| 5,098,388 A | 3/1992 | Kulkashi et al. |
| 5,100,379 A | 3/1992 | Wendell |
| 5,100,390 A | 3/1992 | Lubeck et al. |
| 5,106,376 A | 4/1992 | Mononen et al. |
| 5,119,832 A | 6/1992 | Xavier |
| 5,129,889 A | 7/1992 | Hahn et al. |
| 5,135,525 A | 8/1992 | Biscoping et al. |
| 5,160,323 A | 11/1992 | Andrew |
| 5,163,901 A | 11/1992 | Eldor |
| 5,205,828 A | 4/1993 | Kedem |
| 5,207,647 A | 5/1993 | Phelps |
| 5,209,734 A | 5/1993 | Hurley et al. |
| 5,213,578 A | 5/1993 | Heiliger et al. |
| 5,232,442 A | 8/1993 | Johnson et al. |
| 5,234,406 A | 8/1993 | Drasner et al. |
| 5,257,972 A | 11/1993 | Gurmarnik |
| 5,263,936 A | 11/1993 | Yurino |
| 5,269,769 A | 12/1993 | Dhara et al. |
| 5,292,310 A | 3/1994 | Yoon |
| 5,304,141 A | 4/1994 | Johnson et al. |
| 5,306,239 A | 4/1994 | Gurmarnik et al. |
| 5,312,374 A | 5/1994 | Gurmarnik |
| 5,312,375 A | 5/1994 | Gurmarnik |
| 5,320,610 A | 6/1994 | Yoon |
| 5,328,479 A | 7/1994 | Gurmarnik |
| 5,335,671 A | 8/1994 | Clement |
| 5,368,573 A | 11/1994 | Andrew |
| 5,376,082 A | 12/1994 | Phelps |
| 5,385,561 A | 1/1995 | Cerny |
| 5,392,790 A | 2/1995 | Kanner et al. |
| 5,405,334 A | 4/1995 | Roth et al. |
| 5,417,208 A | 5/1995 | Winkler |
| 5,423,760 A | 6/1995 | Yoon |
| 5,423,770 A | 6/1995 | Yoon |
| 5,425,717 A | 6/1995 | Mohiuddin |
| 5,449,351 A | 9/1995 | Zohmann |
| 5,470,318 A | 11/1995 | Griffith, III et al. |
| 5,480,389 A | 1/1996 | McWha et al. |
| 5,490,845 A | 2/1996 | Racz |
| 5,512,045 A | 4/1996 | Gurchumelidze |
| 5,512,052 A | 4/1996 | Jesch |
| 5,520,652 A | 5/1996 | Peterson |
| 5,542,918 A | 8/1996 | Atkinson |
| 5,569,178 A | 10/1996 | Henley |
| 5,573,519 A | 11/1996 | Zohmann |
| 5,584,820 A | 12/1996 | Gurmarnik |
| 5,591,132 A | 1/1997 | Carrie |
| 5,611,778 A | 3/1997 | Brinon |
| 5,628,734 A | 5/1997 | Hatfalvi |
| 5,630,802 A | 5/1997 | Moellmann et al. |
| 5,637,096 A | 6/1997 | Yoon |
| 5,669,876 A | 9/1997 | Schechter et al. |
| 5,669,882 A | 9/1997 | Pyles |
| 5,672,158 A | 9/1997 | Okada et al. |
| 5,685,852 A | 11/1997 | Turkel et al. |
| 5,725,504 A | 3/1998 | Collins |
| 5,730,754 A | 3/1998 | Obenchain |
| 5,752,969 A | 5/1998 | Cunci et al. |
| 5,779,666 A | 7/1998 | Teirstein |
| 5,779,680 A | 7/1998 | Yoon |
| 5,820,588 A | 10/1998 | Howard, III |
| 5,830,188 A | 11/1998 | Abouleish |
| 5,833,662 A | 11/1998 | Stevens |
| 5,836,914 A | 11/1998 | Houghton |
| 5,836,916 A | 11/1998 | Corn |
| 5,846,226 A | 12/1998 | Urmey |
| 5,853,391 A | 12/1998 | Bell |
| 5,857,996 A | 1/1999 | Snoke |
| 5,871,470 A | 2/1999 | McWha |
| 5,885,217 A | 3/1999 | Gisselberg et al. |
| 5,899,891 A | 5/1999 | Racz |
| 5,941,853 A | 8/1999 | Collins |
| 5,957,881 A | 9/1999 | Peters et al. |
| 5,976,110 A | 11/1999 | Greengrass et al. |
| 6,004,293 A | 12/1999 | Bell |
| 6,068,642 A | 5/2000 | Johnson et al. |
| 6,095,149 A | 8/2000 | Sharkey et al. |
| 6,113,569 A | 9/2000 | Becker |
| 6,179,828 B1 | 1/2001 | Mottola et al. |
| 6,190,370 B1 | 2/2001 | Tsui |
| 6,193,704 B1 | 2/2001 | Winters |
| 6,221,048 B1 | 4/2001 | Phelps |
| 6,224,630 B1 | 5/2001 | Bao et al. |
| 6,245,044 B1 | 6/2001 | Daw et al. |
| 6,273,873 B1 | 8/2001 | Fleischer |
| 6,296,624 B1 | 10/2001 | Gerber et al. |
| 6,298,256 B1 | 10/2001 | Meyer |
| 6,363,273 B1 | 3/2002 | Mastrorio et al. |
| 6,371,943 B1 | 4/2002 | Racz et al. |
| 6,558,353 B2 | 5/2003 | Zohmann |
| 6,572,593 B1 | 6/2003 | Daum |
| 6,592,559 B1 | 7/2003 | Pakter et al. |
| 6,610,066 B2 | 8/2003 | Dinger et al. |
| 6,620,180 B1 | 9/2003 | Bays et al. |
| 6,638,238 B1 | 10/2003 | Weber et al. |
| 6,641,563 B1 | 11/2003 | Vitullo et al. |
| 6,708,489 B2 | 3/2004 | Massey et al. |
| 6,709,418 B1 | 3/2004 | Aboul Hosn et al. |
| 6,764,491 B2 | 7/2004 | Frey et al. |
| 6,899,712 B2 | 5/2005 | Moutafis et al. |
| 6,923,813 B2 | 8/2005 | Phillips et al. |
| 6,925,333 B2 | 8/2005 | Krebs |
| 6,979,317 B2 | 12/2005 | Galt et al. |
| 7,022,109 B1 | 4/2006 | Ditto |
| 7,120,487 B2 | 10/2006 | Nelson |
| 7,181,289 B2 | 2/2007 | Pflueger et al. |
| 7,234,468 B2 | 6/2007 | Johnson et al. |
| 7,244,263 B2 | 7/2007 | Robison et al. |
| 7,318,831 B2 | 1/2008 | Alvarez et al. |
| 7,400,930 B2 | 7/2008 | Sharkey et al. |
| 7,465,278 B2 | 12/2008 | Cicenas et al. |
| 7,632,294 B2 | 12/2009 | Milbodker et al. |
| 7,647,123 B2 | 1/2010 | Sharkey et al. |
| 7,727,186 B2 | 6/2010 | Makower et al. |
| 7,740,631 B2 | 6/2010 | Bleich et al. |
| 7,806,834 B2 | 10/2010 | Beckman et al. |
| 7,819,819 B2 | 10/2010 | Quick et al. |
| 7,828,748 B2 | 11/2010 | Hibner |
| 7,854,706 B2 | 12/2010 | Hibner |
| 7,909,822 B2 | 3/2011 | Guerra |
| 7,918,804 B2 | 4/2011 | Monson et al. |
| 8,016,846 B2 | 9/2011 | McFarlin et al. |
| 8,088,119 B2 | 1/2012 | Saal et al. |
| 2002/0183758 A1 | 12/2002 | Middleton et al. |
| 2003/0176778 A1 | 9/2003 | Messing et al. |
| 2003/0212395 A1 | 11/2003 | Woloszko et al. |
| 2004/0034339 A1 | 2/2004 | Stoller et al. |
| 2004/0049217 A1 | 3/2004 | Ross et al. |
| 2004/0064127 A1 | 4/2004 | Lerner |
| 2004/0092992 A1 | 5/2004 | Adams et al. |

| | | |
|---|---|---|
| 2004/0098006 A1 | 5/2004 | Nakanishi |
| 2004/0102760 A1 | 5/2004 | Hsue et al. |
| 2004/0127963 A1 | 7/2004 | Uchida et al. |
| 2004/0210231 A1 | 10/2004 | Boucher et al. |
| 2004/0267282 A1 | 12/2004 | Shkarubo et al. |
| 2005/0004563 A1 | 1/2005 | Racz et al. |
| 2005/0010205 A1 | 1/2005 | Hovda et al. |
| 2005/0090801 A1 | 4/2005 | Racz et al. |
| 2005/0197661 A1 | 9/2005 | Carrison et al. |
| 2005/0203527 A1 | 9/2005 | Carrison et al. |
| 2005/0234425 A1 | 10/2005 | Miller et al. |
| 2005/0261692 A1 | 11/2005 | Carrison et al. |
| 2006/0004369 A1 | 1/2006 | Patel et al. |
| 2006/0064101 A1 | 3/2006 | Arramon |
| 2006/0110017 A1 | 5/2006 | Tsai et al. |
| 2006/0111728 A1 | 5/2006 | Abdou |
| 2006/0129062 A1 | 6/2006 | Nicoson et al. |
| 2006/0229550 A1 | 10/2006 | Staid et al. |
| 2006/0239982 A1 | 10/2006 | Simpson |
| 2006/0258951 A1 | 11/2006 | Bleich et al. |
| 2006/0264994 A1 | 11/2006 | Schomer et al. |
| 2006/0271196 A1 | 11/2006 | Saal et al. |
| 2006/0271197 A1 | 11/2006 | Saal et al. |
| 2006/0284994 A1 | 12/2006 | Kim |
| 2007/0055259 A1 | 3/2007 | Norton et al. |
| 2007/0162062 A1 | 7/2007 | Norton et al. |
| 2008/0183175 A1 | 7/2008 | Saal et al. |
| 2008/0183192 A1 | 7/2008 | Saal et al. |
| 2008/0188826 A1 | 8/2008 | Saal |
| 2008/0188827 A1 | 8/2008 | Saal |
| 2008/0221586 A1 | 9/2008 | Garcia-Bengochea et al. |
| 2008/0221589 A1 | 9/2008 | Balling et al. |
| 2008/0221605 A1 | 9/2008 | Saal et al. |
| 2008/0255563 A1 | 10/2008 | Farr et al. |
| 2008/0294166 A1 | 11/2008 | Goldin et al. |
| 2008/0294167 A1 | 11/2008 | Schumacher et al. |
| 2009/0048678 A1 | 2/2009 | Saal et al. |
| 2009/0076486 A1 | 3/2009 | Cucin |
| 2009/0216234 A1 | 8/2009 | Farr et al. |
| 2010/0152611 A1 | 6/2010 | Parihar et al. |
| 2011/0054349 A1 | 3/2011 | Hibner |
| 2011/0098596 A1 | 4/2011 | Ozturk et al. |
| 2011/0306879 A1 | 12/2011 | Saal et al. |
| 2012/0004595 A1 | 1/2012 | DuBois et al. |

FOREIGN PATENT DOCUMENTS

| | | |
|---|---|---|
| WO | WO 2008/094436 | 8/2008 |
| WO | WO 2008/094444 | 8/2008 |
| WO | WO 2008/094439 | 9/2008 |
| WO | WO 2008/095177 | 10/2008 |
| WO | WO 2009/052194 | 4/2009 |
| WO | WO 2009/124192 | 10/2009 |
| WO | WO 2012/003383 | 1/2012 |

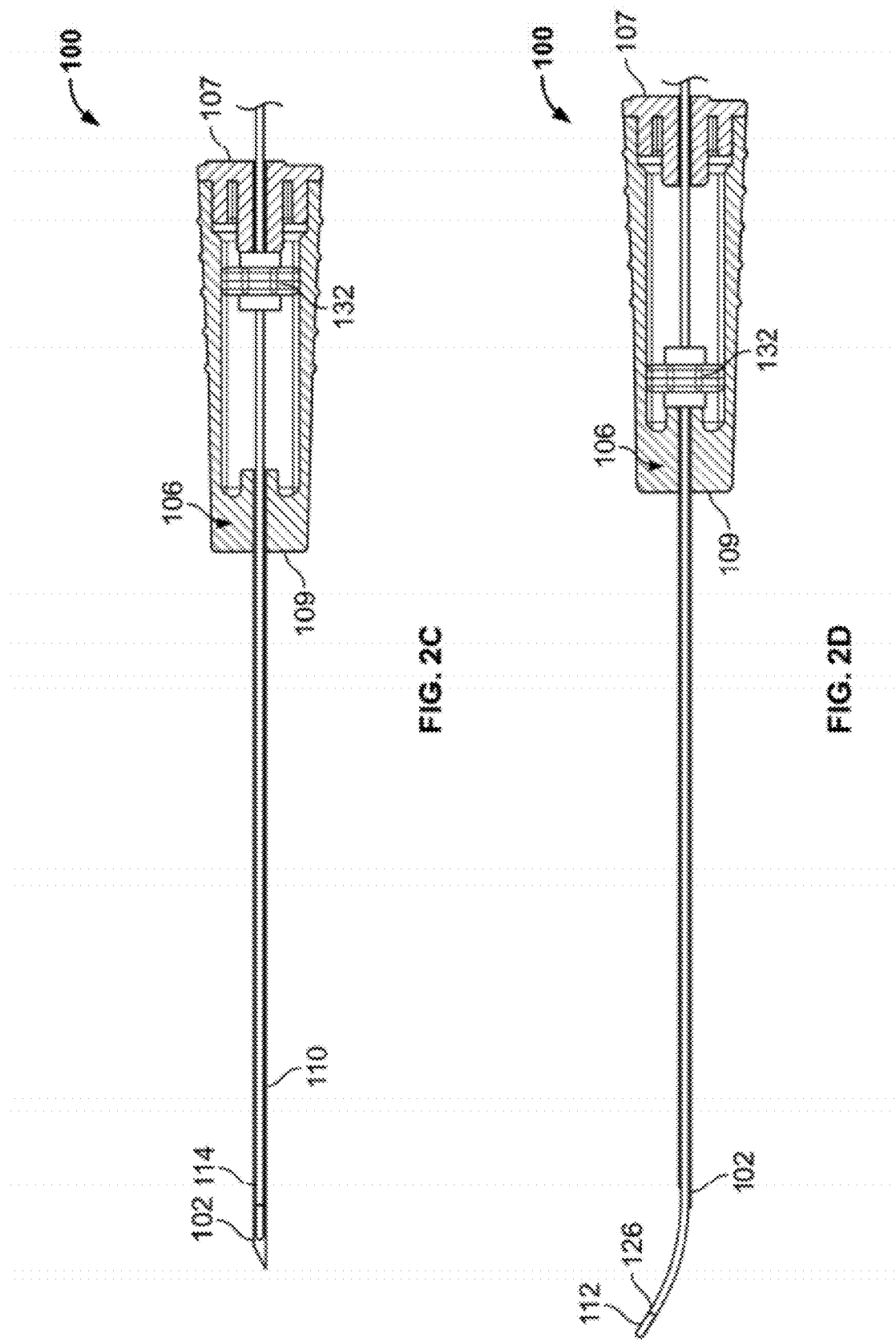

METHOD OF ACCESSING TWO LATERAL RECESSES

RELATED APPLICATIONS

This is a non-provisional application of U.S. Provisional Application No. 61/123,028 filed Apr. 2, 2008. The contents of which are incorporated herein by reference in their entirety.

FIELD OF THE INVENTION

The present invention is drawn to devices and methods for improved injection systems. Variations of the devices and methods of the injection systems provide atraumatic injection delivery within a spinal column while minimizing the likelihood of causing adverse events.

BACKGROUND OF THE INVENTION

Annually, millions of Americans suffer from significant spine related pain and discomfort. Where the cervical, thoracic, and lumbar vertebrae and discs can be the source of this pain and discomfort. In one estimate, pain perceived in the neck or upper limbs that is caused by irritation in the nerves that exit the cervical spine through the foramen affects a population of approximately 1 person per 1000 per year. As a result, every year physicians in the United States perform an estimated 750,000 transforaminal cervical injections to treat these patients.

While the nerve irritation and resultant inflammation causing this spinal pain has a variety of etiologies that result in contact between the nerve and the adjacent structures in the spine, transforaminal injections of corticosteroids can relieve this irritation and reduce the accompanying pain.

Injections of corticosteroids and or local anesthetics into isolated areas of the epidural space are important treatment and diagnostic modalities for patients suffering from spinal pain syndromes. Isolation of the injection to a specific spinal level is accomplished by using a transforaminal approach. This is distinguishable from the traditional trans-laminar approach of spinal epidural injections commonly used for anesthesia.

Presently, physiatrists, anesthesiologists, radiologists, neurologists, and orthopedic surgeons perform such transforaminal injections under fluoroscopic guidance using a C-Arm fluoroscope, a standard spinal needle, and three 3 cc syringes. One current technique in providing these injections includes conscious sedation of the patient through the use of local anesthetic and anxiolytics. The operator performs the procedure using multi-plane fluoroscopy to guide the needle into position and to verify correct location of the delivery device prior to injection of the substance.

As shown in FIG. 1, existing delivery devices include a 20-25 gauge hypodermic needle 1 that is inserted through the skin, muscle and soft tissues 10. Using fluoroscopy, the operator positions the distal end of the needle immediately adjacent to a portion of a vertebral body 12 at the level of the desired injection. Typically when delivering the injection in a cervical region of the spine, this includes positioning the tip of the needle immediately adjacent to a posterior inferior aspect of a superior articular process 14 of a facet joint of the vertebral body 12 at an index foraminal level chosen for the injection. Care must be taken to avoid puncturing the vertebral arteries or veins 16 extending through foramens in the vertebral body 12.

To test the initial placement of the needle it is standard for the operator to initially inject a contrast media, such as a radio opaque dye. This step is useful to determine whether the needle is undesirably located in a blood vessel 16 or in the dural membrane 18. To verify whether the needle is desirably placed, the operator observes under fluoroscope for negative indication of veneous, arterial, or cerebrospinal uptake of the dye. Upon confirming the correct location, the needle is left in position while the syringe containing the radio opaque dye is carefully removed from the needle and replaced by a syringe containing a local anesthetic such as lidocaine. As explained below, the operator must take great care not to avoid any inadvertent movement or advancement of the needle especially during exchange of the syringes.

The operator then injects a small bolus of lidocaine (or a local anesthetic of choice) and waits a sufficient period (e.g., sixty seconds) to allow for the anesthetic to disperse. During this time the operator observes the patient for adverse reactions resulting from accidental vascular uptake or injection into the dural sleeve or thecal sac. Although placement of the needle was observed using the radiopaque dye, there is still a risk of accidental vascular injections because the needle may have moved during the syringe exchange process or simply because vascular perforation was not detected during the radiopaque dye injection.

Once the operator confirms negative adverse reactions, the operator again carefully exchanges syringes to connect a syringe containing a corticosteroid. Finally, the corticosteroid is injected in an effort to reduce inflammation thereby affording the patient pain relief. After the three injections i.e. radio-opaque dye, local anesthetic, corticosteroid are complete, the needle is removed from the patient.

Although the current procedure provides benefits to patients having spinal related pain, significant risk remains with the current procedure. One inherent risk includes breaching a blood vessel and the inadvertent injection of dye, anesthetic, and/or corticosteroids into an artery or vein. Currently, it is believed that breaching a blood vessel occurs in a considerable number of injections performed (a recent clinical study had venous uptake in over 19% of injections performed). Additional risks include contact between the injection needle and the nerve root, which may cause pain along with damage to the dura. Finally, there are risks associated to the operator via exposure to the X-Ray radiation of the fluoroscope, particularly in view of the cumulative exposure as the operator must position the needle as well as exchange syringes a number of times.

The actual breaching of the blood vessel may occur during the initial insertion of the needle into the site, subsequent manipulation of the needle during syringe exchanges, or even movement of the needle as a result of the force applied by the operator during actuation of the syringe. In some cases, injection into a blood vessel may occur even if the needle has not penetrated the vessel wall as the force of the injectant flowing out of the distal tip of the needle can be sufficient cause the injectant to breach the blood vessel wall and enter into the vessel.

Complications from accidental injection of the anesthetic into the vessel can include transient paralysis of the spinal cord. Complications resulting from accidental injections of corticosteroids into blood vessels can include permanent paralysis, permanent blindness (if injected into a vertebral artery), seizures, permanent cognitive dysfunction, physical impairment, and/or death.

Another complication associated with transforaminal injections is inadvertent contact between the needle and nerve root which may cause pain or tingling emanating through the upper extremities. If the needle perforates the dural sleeve, spinal fluid may leak resulting in a transient headache lasting from several hours to several days. If local anesthetic is injected into the thecal sac, temporary paralysis may occur that could result in a cessation of breathing, necessitating emergency incubation of the patient.

In view of the above risks, to ensure patient safety the operator must reposition the needle if he or she suspects that patient harm could occur. In addition, if arterial uptake is suspected, a common recommendation is that the procedure should be abandoned to allow the arterial perforation to heal and to obviate the risk of injury to the spinal cord resulting from inadvertent injection of corticosteroid into the radicular artery or vertebral artery.

Each time the needle is repositioned, a new X-Ray image must be captured to verify the needle position and additional real time fluoroscopy images must be captured with an additional injection of contrast media. The additional fluoroscopy and associated radiation exposure presents an increased risk to the operator performing the procedure. To minimize exposure the operator must step toward and away from the radiation field to alternately maneuver or manipulate the hypodermic syringe and allow fluoroscopic images to be taken. This exertion combined with the repeated connecting and disconnecting of syringes contributes to operator fatigue, which is not a trivial consideration for operators performing multiple procedures in a particular day.

In addition to cervical injections, patients typically require treatment of more than one vertebral level. One procedure for performing injections at adjacent vertebral levels is to position multiple needles simultaneously. This enables the physician to adjust the position of both needles with a single fluoroscopic image, thus saving time and reducing the number of fluoroscopic images required as compared to doing each level individually. Alternatively, the physician may perform the injection at each vertebral level sequentially by positioning the needle at the injection site of one vertebral level and withdrawing the needle before commencing placement of a needle at the second vertebral level.

The design of the current devices presents an additional problem that contributes to undesired device placement. Current devices include rigid and straight hypodermic needles. Such a configuration limits the operator to only work within the "line of sight" from the surface of the skin along an axis of the needle. In many cases, it is desirable to perform the injection in a position that is not directly accessible by a straight, rigid needle, e.g., it is frequently desirable to inject medicine in a position "behind" portions of the vertebra, nerves, or blood vessels, (i.e. around the corner from the line of sight position).

In some cases, a physician will want to access a treatment location for a lumbar transforaminal epidural injection that is along the nerve root in a lateral recess within the vertebral body. The nerve resides in the lateral recess and typically is impacted by either stenosis or disc herniation. In such cases, the impinged nerve cannot be accessed with straight needle based techniques. This site of neuropathology is ideal for the treatment of pain resulting from an inflamed nerve root; however it is inaccessible when using a straight needle. Therefore, conventional procedures force the physician to position the distal tip of the straight needle outside the foramen adjacent to the pedicle and exiting nerve root. Knowing that the conventional needle is spaced from the desired location, the physician performs the injection presuming flow in the superior lateral recess, (i.e. a transforaminal injection at the L5-S1 foramen will place medication around the exiting L5 nerve root and to a degree into the lateral recess where L5 nerve traverses through prior to exiting). In most cases, only a small amount of medication injected flows into the site of pathology.

In many cases, the physician causes nerve trauma by contacting the nerve with the tip of the needle when entering the foramen. This is especially common in cases of spinal stenosis, collapsing degenerative scoliosis, and deep seated L5-S1 segments with high pelvic brims. Such nerve trauma leads to acute patient discomfort, often leading to vaso-vagal type hypotensive reactions, and at the minimum requires the operator to re-position the needle to gain acceptable injection access without causing undue nerve pain. Overly sedating the patient to control this problem often only leads to increased nerve root trauma and a high likelihood of a neuropathic pain following the procedure.

Accidental vascular intrusion is believed to occur in >15% of lumbar cases. While intra-vascular injection in the lumbar spine is not associated with catastrophic complications as in the cervical area, it will cause transient hypotension leading to vaso-vagal attacks, and the necessity to reposition needle to avoid the vascular elements. This phenomenon leads to increased work time for the physician, and increased patient discomfort and morbidity.

Devices and methods are provided herein for a transforaminal epidural injection needle system that minimizes the above risks to improve patient safety. In addition, the benefits of such devices reduce operator fatigue and decrease the operator's potential radiation exposure.

The methods and devices may be used for transforaminal selective epidural injections to the cervical, thoracic, or lumbar spine. Fluoroscopically guided, contrast-enhanced transforaminal epidural injection procedures help to specifically evaluate and treat the precise spinal nerve involved as a source of spinal and referred extremity pain. Although therapeutic and diagnostic transforaminal epidural injections have been performed for decades, the equipment used for these injections has been relatively unchanged during that time.

SUMMARY OF THE INVENTION

The present invention incorporates features that address each of the risks listed above. The devices and methods described herein include a catheter with a blunt distal tip and an injection port that allow drugs or other substances to disperse at a target site while minimizing safety concerns. The construction of the catheter decreases the chances of inadvertently injecting substances into a blood vessel as well as inadvertently damaging structures because of incorrect placement of a needle.

The invention includes an injection system comprising a needle cannula having a sharp tip at a far end of the needle cannula, where the sharp tip is adapted to penetrate tissue, and a needle lumen extending through needle cannula. The device includes a sliding member slidably affixed within the needle lumen to move between a retracted position and a deployed position within the needle lumen. This sliding member may be a plunger, a stop surface, or any such structure. In additional variations, the sliding member can be non-rotational (e.g., such as having a groove or keyway) so that the injection tube injection port is always oriented relative to the cannula Alternatively, the sliding member can rely on keys, indents, detents, etc. so that the sliding member is rotatable to less than 360 degrees allowing for rotation of the injection tubing. In yet another variation, the sliding member can provide information relating to the orientation of the catheter tubing to the physician via markings, etc. An injection tubing having a distal portion having a distal end, a proximal portion, and an injection lumen extending between the distal portion and the proximal portion, where the injection lumen exits the injection tubing at an injection port located in a sidewall in the distal portion; where the injection tubing is affixed to the sliding member such that when the sliding member is in the proximal position, the distal portion is within the needle cannula and when the sliding member advances to the deployed position, the distal portion of the injection tubing extends out of the far end of the needle cannula. Given that the sliding member is affixed to the injection tubing, the injection tubing can be moved a limited distance by advancement or retraction of the sliding assembly. The benefits of such a feature are described below. An embodiment of the system also includes a plurality of independent extension tube lumens where a manifold fluidly couples each of the extension tube lumens to the injection lumen.

The invention further includes methods of delivering substances into an epidural space using one of the variations of the devices described. In one variation the invention includes methods of delivering substances into a spine, epidural space, spinal canal or similar region of the body.

The methods, systems and devices permit the physician to access lateral recesses in vertebral bodies directly. This allows the delivery of medication directly at the source of pathology. The present methods, systems and devices enable the physician to position a tip of a needle safely away from the exiting nerve root prior to advancing a flexible, curved, elastic catheter into the foramen and lateral recess to inject the medication directly into the site of pathology. The injection tube described herein (typically a small caliber catheter) traverses the foramen, thereby eliminating or dramatically reducing the incidence of nerve root contact and the associated sequelae as discussed above. In addition, the physician can determine the path of travel from outside of the body either by visual indicators or tactile indicators.

In one variation, the system includes a needle cannula having a needle lumen extending therethrough, the needle cannula has an axis; an injection tubing having a distal portion, a distal end, a proximal portion, and an injection lumen extending through at least the distal portion, an injection port in fluid communication with the injection lumen and located on a section of the distal portion that is spaced proximally from the distal end such that the fluid medium exits laterally to the section, where at least the distal portion is flexible and curves when advanced from the needle cannula such that upon advancement out of the needle cannula the distal end of the injection tubing moves away from an axis of the needle cannula, where the injection tubing is non-rotational but axially moveable within the needle lumen; a sliding member affixed to the injection tube such that a sliding movement of the injection tubing limits a stroke of the injection tubing to the fixed distance such that when the injection tubing is in the proximal position, the distal portion is within the needle cannula and when the injection tubing advances to the deployed position, the distal portion of the injection tubing extends out of the far end of the needle cannula; and a connector on the proximal portion of the injection tube for coupling the injection tube to a fluid source.

In an additional variation, the system includes a needle cannula having a needle lumen extending there through, the needle cannula having an axis; a injection tubing having a distal portion, a distal end, a proximal portion, and an injection lumen extending through at least the distal portion, where at least the distal portion is flexible and curved such that upon advancement out of the needle cannula the distal end of the injection tubing assumes the curved shape such that the distal end moves away from an axis of the needle cannula, where the injection lumen is in fluid communication with an injection port that is spaced proximally from the distal end such that the medium exits in a lateral direction, where the injection tubing is rotationally and axially moveable within the needle lumen and limited to extend out of the needle lumen by a fixed distance; a sliding member affixed to the injection tube such that a sliding movement of the injection tubing limits the injection tubing to the fixed distance such that when the injection tubing is in the proximal position, the distal portion is within the needle cannula and when the injection tubing advances to the deployed position, the distal portion of the injection tubing extends out of the far end or the needle cannula; a directional indicator located on the sliding member, where the directional indicator indicates the direction in which the distal end of the injection tubing moves away from the axis of the needle; and a connector on the proximal portion of the injection tube for coupling the injection tube to a fluid source.

The variations of the injection systems described herein can include one or more directional indicators located on the needle cannula, where the directional indicator indicates the direction in which die distal end of the injection tubing moves away from the axis of the needle. In additional variations, directional indicator(s) can be located on the injection tubing rather than the needle lumen or hub.

The directional indicators can further include a visual mark and/or a tactile protrusion extending in a direction relative to the curve such that an operator can track direction of the curve by feeling the tactile protrusion.

The injection ports used in the present systems can be located on any portion of the injection tube. However, in many variations, one or more injection ports shall be located on an interior and/or exterior of the curve.

The systems can include additional safety features to minimize inadvertent shearing of the injection tube by the needle. For example, the needle tip can include a bevel tissue piercing shape having a heel at a proximal end. In some variations, the heel can include a recessed section that minimizes engagement between the heel and the injection tubing. Additional features include at least one wire located within the injection lumen. Where one or more wires can be a radiopaque wire, a shape memory alloy or a super elastic alloy (or a combination thereof).

The disclosure further includes methods of delivering one or more substances at an injection site near a vertebral body in a patient, where the method includes providing an injection system including a needle cannula having a needle lumen extending therethrough and an injection tubing having a curved shape at a distal portion, where the injection tube is slidably located in the needle lumen to move between a retracted position and a deployed position, where in the retracted position the injection tubing remains within the within the needle lumen and in the deployed position the injection tubing extends out of a far end of the needle cannula such that the curved shape causes an end of the injection tubing to move away from an axis of the needle cannula, where an rotational indicator on the needle cannula correlates to the direction of movement of the end of the injection tubing; inserting a tip of the needle cannula into the patient so that the tip is positioned adjacent to the vertebral body: advancing the distal end of the injection tube around a feature of the vertebral body into a vertebral foramen by advancing the injection tube within the needle cannula such that the distal portion exits the injection tube and assumes the curved shape to advance into a first lateral recess within the vertebral body; delivering at least a first substance at the first lateral recess; retracting the injection tube within the needle cannula without withdrawing the cannula from the body; rotating the needle cannula using the rotational indicator to rotationally position the needle cannula; and advancing the injection tube within the needle cannula such that the distal portion exits the injection tube and assumes the curved shape to advance into a second lateral recess within the vertebral body, where the second lateral recess is directionally opposite or adjacent to the first lateral recess.

In an additional variation, a method of delivering injections to multiple lumbar sites with a single needle insertion can include providing an injection system including a needle cannula having a needle lumen extending therethrough and an injection tubing having a curved shape at a distal portion, where the injection tube is slidably located in the needle lumen to move between a retracted position and a deployed position, where in the retracted position the injection tubing remains within the needle lumen and in the deployed position the injection tubing extends out of a far end of the needle cannula such that the curved shape causes an end of the injection tubing to move away from an axis of the needle cannula, where an rotational indicator on the needle cannula correlates to the direction of movement of the end of the injection tubing; inserting a tip of the needle cannula into the patient so that the tip is positioned adjacent to the vertebral body, advancing the distal end of the injection tube around a feature of the vertebral body into a vertebral foramen by advancing the injection tube within the needle cannula such that the distal portion exits the injection tube and assumes the curved shape to advance into a first lateral recess within the vertebral body; retracting the injection tube within the needle cannula without withdrawing the cannula from the body; rotating the injection tubing using the rotational indicator to rotationally position the needle cannula; and advancing the injection tube within the needle cannula such that the distal portion exits the injection tube and assumes the curved shape to advance into a second lateral recess within the vertebral body, where the second lateral recess is anatomically superior or inferior to the first lateral recess.

In any of the methods described herein, the injection tubing can have a flexible or floppy distal portion so that as the device advances out of the needle cannula, the distal portion assumes a curve when encountering structures or tissues in the body.

Variations of the methods include retracting the injection tube then repositioning the needle cannula without removing the needle cannula from the body.

In additional variations, using the rotational indicator to rotationally position the needle cannula can include feeling a tactile feature on the rotational indicator to align the needle cannula with a desired orientation.

The injection system may deliver injectants, injectable substances, and/or injectable fluids. Such substances are intended to include any medication or diagnostic fluid the physician (or operator) may choose to administer with the system.

It is noted that the invention includes combinations of embodiments or aspects of the embodiments themselves. The following illustrations are intended to convey an overall concept of the inventive methods and devices.

BRIEF DESCRIPTION OF THE DRAWINGS

The invention is best understood from the detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 2C shows a cross sectional view of another variation of an injection system without a plunger mechanism.

FIG. 2D shows a cross sectional view of the injection system of FIG. 2C where the catheter or injection tube is advanced out of the needle cannula.

DESCRIPTION OF THE INVENTION

Figure 1:
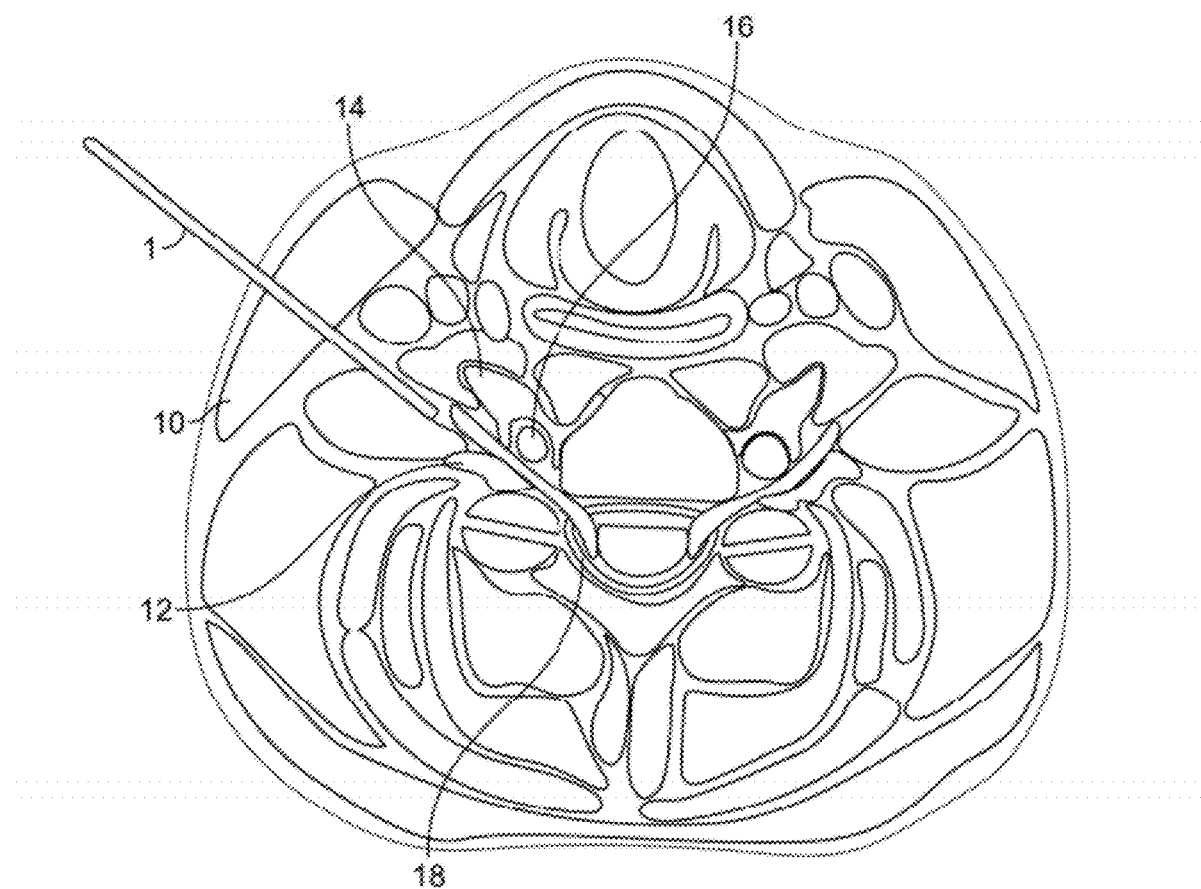
FIG. 1 illustrates a previously known procedure for injecting a substance within a spinal canal of a patient.

FIG. 1 illustrates a variation of an injection system 100. Although the systems and methods described herein are often described as being used as a cervical injection system or for the cervical region of the spine, the device and methods may be applied in a broader and to various other parts of the spine as well as anatomic structures where the features of the system may provide useful.

As shown in FIG. 1, the system 100 includes a cannula or needle cannula 102 where a distal tip 104 of the needle cannula 102 is sharp so that an operator may advance the cannula 102 through tissue to reach the intended target site. The needle cannula 102 may optionally include a hub 106. The hub 106 may be a common polymeric hub that is molded, bonded, or otherwise affixed to the needle cannula 102. Alternatively, though not shown, the hub 106 may comprise a section of the needle cannula 102 itself. In any case, in some variations of the system 100, the hub 106 provides an ergonomic surface for the operator to grip during insertion and potentially manipulate with a single hand. The shape of the hub (and device body as described in additional variations below) should enable the operator to hold the hub and/or device between their thumb and forefinger of each hand. This improves the operator's ability to aim and guide the needle (and ultimately the catheter/injection tubing) into position. Additionally, this design shape allows the operator excellent tactile feedback during insertion of the device and advancement of the injection tubing.

In one example, when the system 100 is optimized for use in delivering injections in the spinal area, the needle cannula can be any standard needle. In spinal applications the cannula can be 19 to 26 gauge. In one variation useful for cervical region treatment, a 22 Ga needle having a length of 2.5 inches was developed. However, alternative variations of the invention include needles of varying lengths, gauges, as well as cross-sectional shape. As shown, the needle cannula 102 extends only partially into the hub 106. However, variations also include a needle cannula 102 that extends through the hub 106.

In any case, the needle cannula 102 includes a needle lumen 108 through which a catheter or injection tubing 110 extends. Although not illustrated, the injection tubing 110 includes an injection lumen extending therethrough and exiting at an injection port 112 in a wall at a distal portion 114 of the injection tubing 110. In additional variations, the device can include an injection port at a distal end of the injection tubing 110. In addition, variations of devices disclosed herein can include more than one injection port.

The injection tubing 110 can be made of a flexible material such as any polymeric or composite material used for medical device applications. In addition, the catheter tubing can have elastic characteristics (e.g., flexible polymers, coil or other reinforced catheters, or super-elastic/shape memory characteristics), that allow the device to curve slightly around or deflect away from structures such as blood vessels, nerves, or bone to optimally position the orifice for the injections.

The elastic characteristics may come from the properties of the tube, an elastic wire that is extruded within the wall of the tube, or even an elastic stylus that temporarily resides in the lumen of the tubing. In some variations of the system, the curve of the distal portion of the catheter tubing also enables the operator to "steer" the catheter by orienting the distal tip such that the catheter tends to follow a particular direction.

Placing the injection port 112 in a side wall and not at a distal end 120 prevents the likelihood that fluid ejected from the device 100 will cause inadvertent damage to the patient. For example, even if a distal tip 120 of the system 100 pierces a vessel or the dura, then the proximal spacing of the injection port 112 reduces the likelihood that the injected fluid would actually enter the structure as the fluid will be injected proximal to the entry point. In other words, it would be necessary for the entire distal portion 114 of the injection tubing 110 (from the injection port 112 to the distal tip 120 to cannulate the vessel or dura. In the variation shown, the injection tubing 110 also includes one or more visualization marker(s) 125. For example, a single radiopaque marker 125 can be placed adjacent to the injection port 112 so that the operator may precisely locate the proximity of the injection port 112 to a vessel or other structure. Yet another feature that improves safety is placement of the injection port 112 on an interior radius or aspect of the curved distal portion 114 of the injection tubing 110. As fluid disperses from the injection port 112, because the injection port 112 is on the interior curve of the distal portion 114 of the injection tubing 110, the fluid is delivered away from the dura or other nerve structures (as will be discussed below). However, additional variations of the invention contemplate placing an injection port 112 anywhere along the distal portion of the injection tubing 110.

Systems 100 of the present invention also include a sliding member, in this variation the sliding member is a plunger 122 slidably affixed within a lumen of the needle cannula 102 and secured to the injection tubing 110. This construction permits movement of the plunger 122 to advance or retract the injection tubing 110. Since the plunger 122 is slidably affixed within the needle cannula 102, the plunger 122 can move between a proximal or retracted position (where the distal portion 114 of the injection tubing is retracted within the needle cannula) and a distal or deployed position (where the distal portion 114 of the injection tubing 110 is deployed from the needle cannula 102 as shown in FIG. 2A).

Figure 2B:
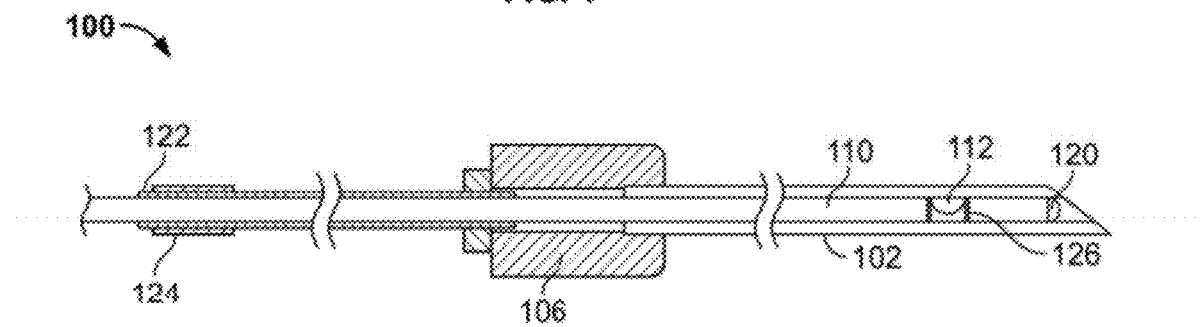
FIG. 2B shows a cross sectional view of the injection system of FIG. 2A where the catheter or injection tube is withdrawn into the needle cannula.

FIG. 2B illustrates a distal section of the system 100 showing the plunger 122 in a retracted position causing the distal portion 114 of the injection tubing 110 as well as the injection port 112 withdrawn into the cannula 102. As discussed below, configuring the injection tubing 110 to advance in and out of the cannula 102 improves the ability of the operator to safely locate the tip 104 of the cannula 102 while advancing the injection tubing 110 and port 112 to a desired location for delivery of the substances. This feature of the system 100 is discussed in further detail below. Alternate variations of the invention can include plungers that are removeable from the needle cannula 102. The plunger 122 may comprise a simple tube structure. In some variations of the system 100, the fit between the injection tubing 110 and needle cannula 102 allows a tactile "feel" of the resistance as the catheter is advanced to the injection site. This feature helps the operator feel whether the tip of the device encounters any strictures as it advances to the target site.

Figure 2A:
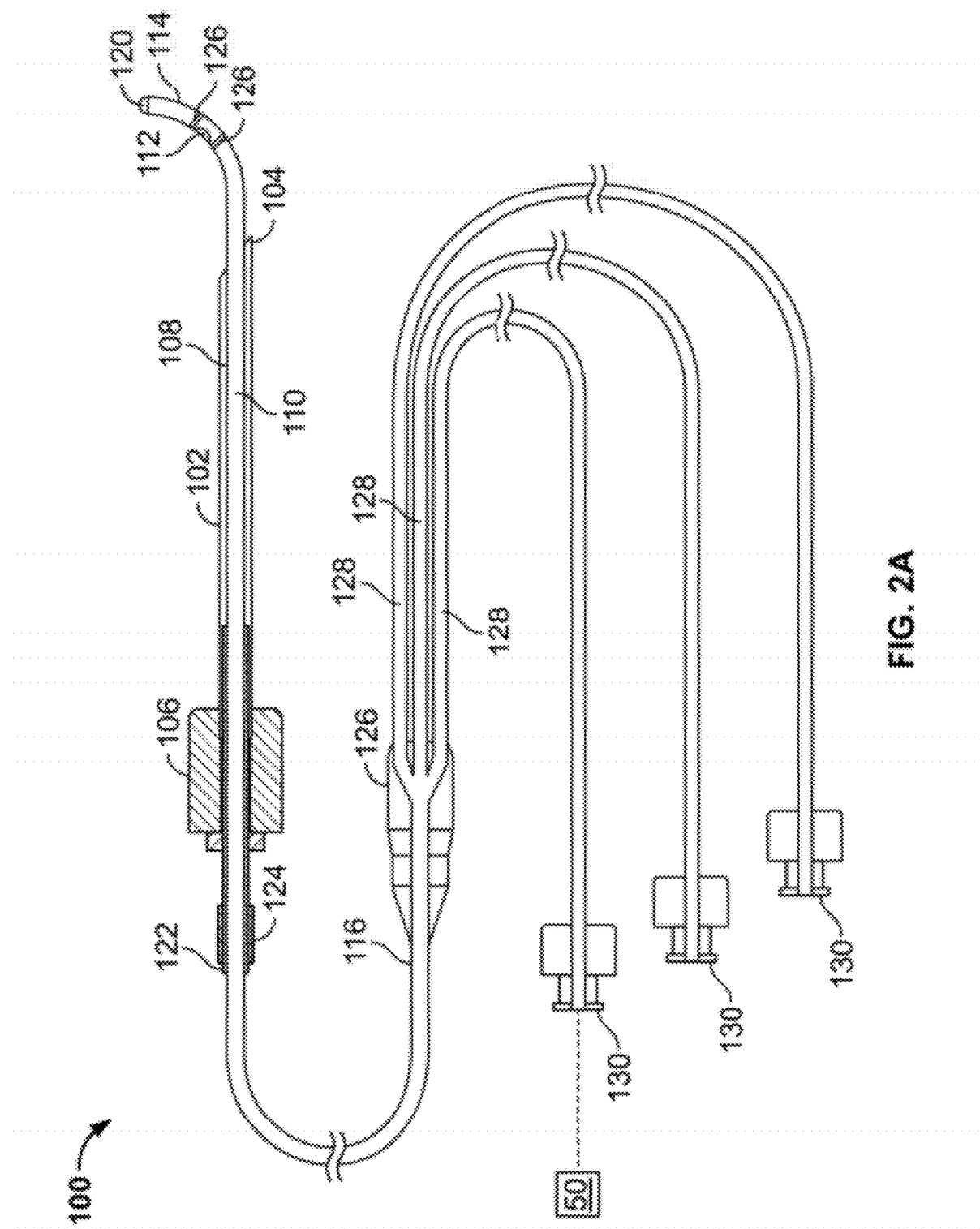
FIG. 2A shows a cross sectional view of an example an injection system incorporating the concepts discussed herein.

In the variation shown in FIG. 2A a proximal portion 116 of the injection tubing 110 extends from the plunger 122 to a manifold 126. The manifold 126 allows fluid coupling of any number of extension tubes 128 having separate lumens to the lumen of the injection tubing 110. Although the variation shows three separate extension tubes 128, variations of the device may include a single extension tube with a plurality of independent lumens. The independent lumens should allow coupling of the system 100 to independent fluid sources 50 (typically syringes or other such storage vessels). The number of lumens may be any number greater than 1. However, when the system 100 is used for treatment of spinal conditions, the system 100 will typically include three separate extension lumens so that three separate fluid sources (e.g., a source of a contrast agent, a source of an anesthetic, and a source of an anti-inflammatory substance such as a corticosteroid). As shown, the extension tube 128 can include a luer or other fitting 130 on the proximal end to allow coupling to a fluid source. Moreover, variations of the device include use of a valve fitting 130 to prevent retrograde flow between syringes.

One advantage of having separate lumens for coupling syringes or fluid sources is to maintain segregation between the injectable substances. The use of multiple tube lumens reduces the amount of residual substances that must clear the device during subsequent injections. This reduces risk of injecting the patient with an excessive amount of any substance or inadvertent injection of an incorrect substance.

In certain variations of the system 100, the length from the plunger 122 to the fittings 130 is sufficient so that fluid sources (e.g., syringes) can be coupled to the system 100 and set aside prior to insertion of the needle cannula 102 into a patient. In addition, a sufficient length allows the operator to inject the fluids without excessive exposure to radiation generated by x-ray or fluoroscopic equipment. Although not shown, variations of the system 100 include the use of strain relief sleeves or collars to prevent crimping or folding of the injection tubing 110 at or near the end of the plunger 122.

The operator prepares the system 100 for the procedure by attaching three syringes to the device simultaneously prior to insertion into the patient. Naturally, an operator may choose to attach the syringes to the system 100 after injection of the cannula into the patient; however, this increases the chance of movement of the cannula subsequent to initial placement. The injection tubing 110 is advanced distally from the tip of the needle (as shown in FIG. 2A) and air is purged from the all of fluid lines by actuating the syringes containing the substances to be injected (e.g., corticosteroid, anesthetic, and contrast media). Naturally, the injection tube lumen should be charged with the first substance to be injected into the patient.

The individual syringes can contain a contrast agent such as a radio-opaque dye, a local anesthetic such as Lidocaine, and a corticosteroid. Alternatively, any plurality of lumens and extension tubes could be use in this method were it practical or to the advantage of the operator to have a separate delivery of a plurality of other substances/injectants other than those mentioned above.

After the purging and charging sequences are completed, the injection tubing 110 is retracted into the needle cannula 102 and the operator may now insert the cannula 102 into a patient to provide treatment.

FIGS. 2C and 2D illustrate another variation of a distal section of the system 100 where the sliding member comprises a stop surface 132 that is entirely within the hub 106 of the device 100. FIG. 2C illustrates the plunger 122 in a retracted position causing the distal portion 114 of the injection tubing 110 as well as the injection port 112 to be withdrawn into the cannula 102. As illustrated, the stop surface 132 is affixed to the injection tubing 110 and is slidably moveable within the hub 106. As shown, when the stop surface 132 is retracted towards a proximal portion 107 of the hub 106, the internal construction of the hub 106 prevents further withdrawal of the injection tubing 110 since the stop surface is affixed thereto. As noted above, the stop surface 132 can include a key/groove interface with the interior of the hub to prevent rotation of the injection tubing. Alternatively, the sliding member can rely on keys, indents, detents, etc. so that the sliding member is rotatable to less than 360 degrees allowing for rotation of the injection tubing.

FIG. 2D illustrate distal advancement of the stop surface 132 against a distal portion 109 of the hub 106. Again, since the stop surface 132 is affixed to the injection tubing, distal advancement of the injection tubing 110 is prevented once the stop surface 132 encounters the hub 106. As shown, in the distal most position, the injection tubing extends from the cannula 102 (and optionally curves as shown).

In those variations, where the injection tubing 110 does not include a plunger, the physician simply advances the injection tubing, manifold, or extension lines, to advance a distal portion 114 of the injection tubing from the cannula 102. As noted above, the variation shown in FIGS. 2C and 2D can include a single injection or extension tube, or may include a number of injection tubes fluidly coupled to a lumen of the injection tube.

Figure 3A:
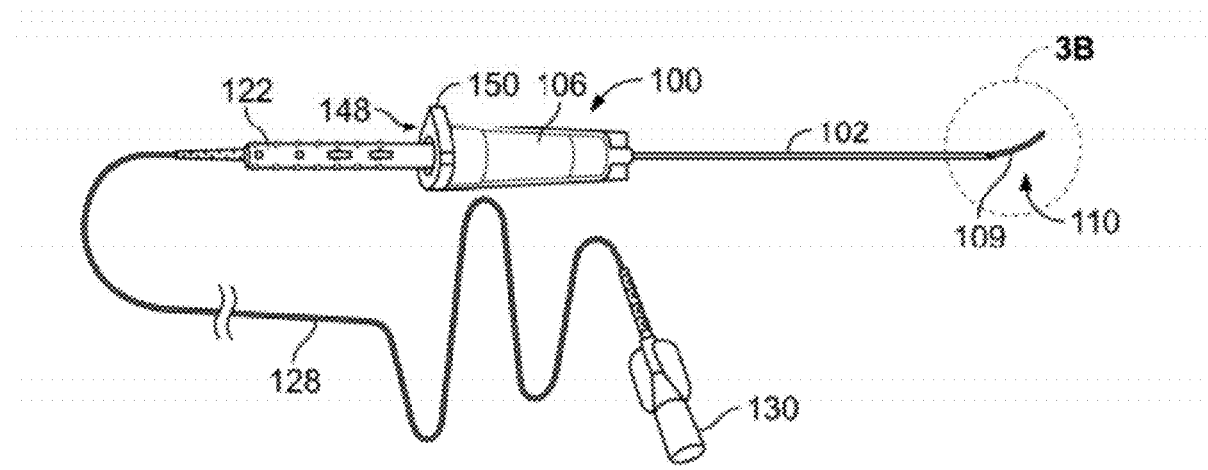
FIGS. 3A to 3C illustrate an additional variation of an injection system.

FIG. 3A illustrates another variation of an injection system 100. As illustrated, the injection system includes a needle cannula 102 having a needle lumen extending through all or a portion of the cannula. This variation of the device includes a hub 106 located on the proximal end of the needle cannula 102. However, other variations of the device (as discussed herein can be combined with the variation shown in FIG. 3A).

The device of FIG. 3A also includes an injection tubing 110 extending through the needle cannula 102 with a distal portion 109 of the tubing 110 terminating at a distal end. The injection tubing 110 includes an injection lumen extending through all or most of the injection tubing 110. The injection lumen is also in fluid communication with an extension line 128. The extension line 128 can be coupled to a fluid source (not shown) via a hub 130 or other connection. As shown, the injection lumen 110 can also include a plunger/slider member 122 or other raised surface that allows a physician to advance and retract the catheter from the distal end of the needle cannula.

Figure 3B:
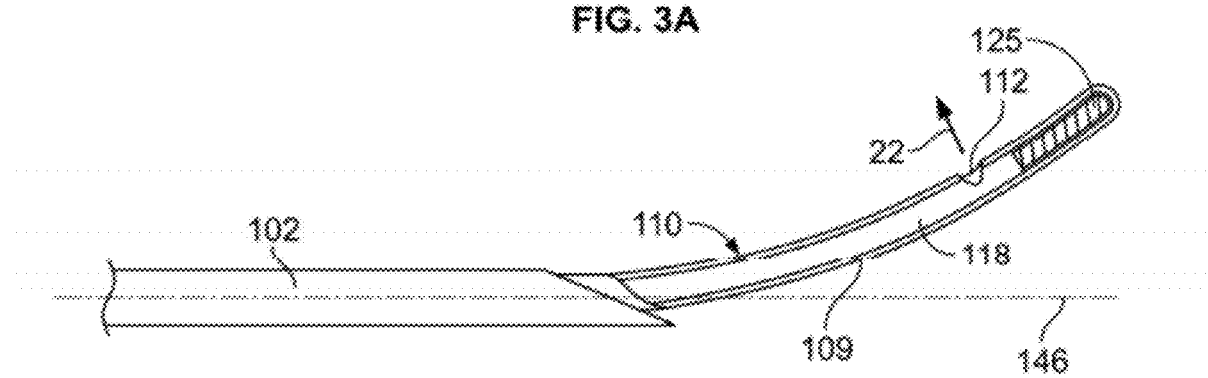
Figure 3C:
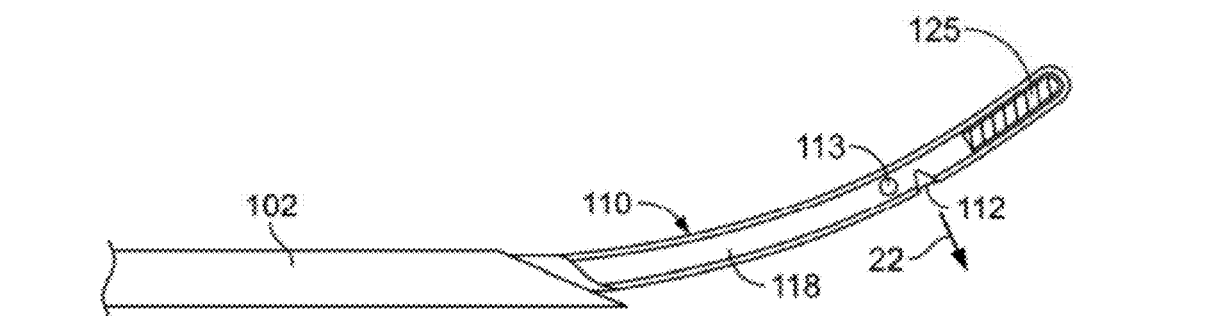

FIGS. 3B and 3C illustrate magnified working ends of two variations of injection tubing 110 for use with injection systems 100 as shown by section 3B in FIG. 3A. As illustrated in FIGS. 3B and 3C, the injection system 100 can deliver injectable medium to the target site via an injection port 112 that is in fluid communication with the injection lumen 118 and located on a section of the distal portion 109 that is spaced proximally from the distal end. In this way, the fluid medium exits laterally to the injection port 112 (or more appropriately, laterally to the section of the injection tube 110 containing the fluid port 112) as shown by arrow 122.

As discussed above, the injection tubing 110 includes a portion (in this case, the distal portion 109) that is flexible and has a curve. Upon advancement out of the needle cannula, the distal portion of the injection tubing 110 curves and moves away from an axis of the needle cannula 102. This curve can be pre-set to allow the device to advance behind bony vertebral structures or around nerves to deliver the fluid medium in a desired target location. Moreover, the distal portion of the injection tubing can be readily deformable or soft such that it curves upon engagement of tissue such as nerves, bony structures, or other objects in the body. As shown in FIG. 3B, the injection port 112 can be on the interior curve or radius of the injection tubing's 110 curved portion 109. Alternatively, as shown in FIG. 3C, the injection port 112 can be on the exterior curve or radius of the injection tubing's 110 curved portion 109. In additional variations, an injection system 100 can have one or more ports on a side and/or both interior and exterior curved portions of the injection tubing 110. As illustration of an alternate variation, an injection port 113 can be additionally, or alternatively located on a side of the curved portion rather than the interior or exterior of the curve.

FIGS. 3B and 3C also illustrate the injection port 112 being adjacent to a radiopaque marker 125. The radiopaque marker 125 permits non-invasive imaging of the tip of the injection tubing 110. Although variations of the system 100 include placement or one or more visualization markers 125 along the injection tubing 110 or needle cannula 102, the illustrated variation shows a visualization marker 125 placed at the distal end of the injection tubing 110 so that the physician can determine, under fluoroscopic imaging, when the injection port 112 is desirably placed within a foramen for delivery of the fluid medium.

In a first variation, the sliding member (as shown in FIGS. 2C and 2D) prevents the injection tubing 110 from rotating within the needle cannula but permit axial movement within the needle cannula 102. This means that the injection tubing 110 can axially translate within the needle cannula 102 but not rotate. In alternate variations, the injection tubing 110 can rotate within the needle cannula 102 but where the rotation will be controlled as noted below.

Again, referring to FIGS. 2C and 2D, the injection tubing 110 can include a sliding member affixed to the injection the such that a sliding movement of the injection tubing limits a stroke of the injection tubing to a fixed distance such that when the injection tubing is in the proximal-most position, the distal portion is within the needle cannula 102 and when the injection tubing 110 advances to the deployed position, the distal portion 109 of the injection tubing 110 extends out of the far end of the needle cannula and advances away from an axis 146 of the needle cannula due to the curved shape. In the variation shown in FIG. 3A, the injection tubing is coupled to a plunger/slider member 122 that provides an area of a raised surface area and provides a handle or hub to move the injection tubing 110 relative to the needle cannula 102.

Figure 5:
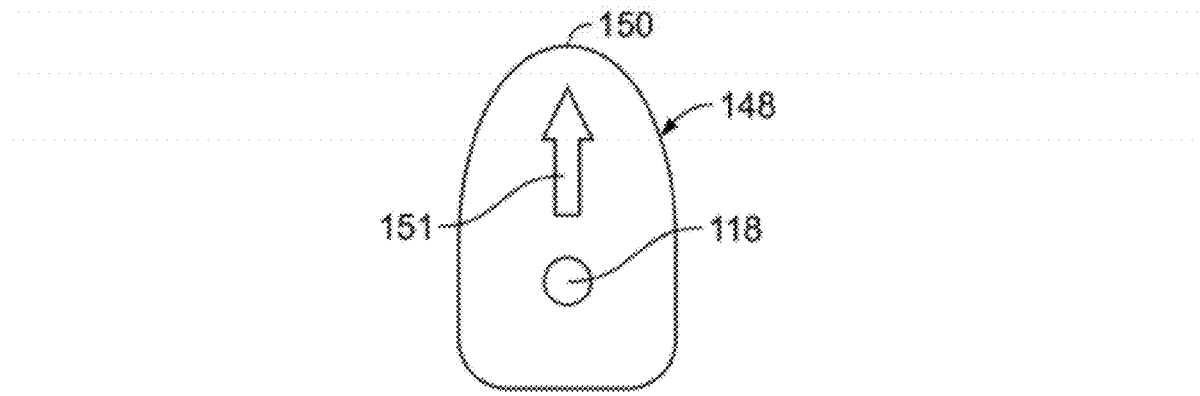
FIG. 5 illustrate an example of a directional indicator with a tactile protrusion that allows a physician to identify the direction of advancement of the curved portion of the injection tubing.

Regardless of whether the injection tubing 110 is rotatable or not, the device 100 can include a directional indicator 148 so that a physician using the device 100 can determine the direction of curvature/path of the curved portion 109 of the injection tubing 110 as it advances from the needle cannula 102. As shown in FIG. 5, the directional indicator 148 provides the information without the need for direct visual sight of the distal tip of the needle cannula 102 (for example, in those cases where the needle cannula 102 is inserted into tissue.) Moreover, variations of the system 100 can include a tactile protrusion 150 on the directional indicator 140. The tactile protrusion 150 conveys the direction of curvature or advancement of the distal portion of the injection tubing 110 through feel alone. For example, in many procedures, the physician may not be able to directly visually observe markers on the system 100. In such cases, the directional indicator and tactile protrusion allow the physician to plan advancement of the injection tubing 110 by feeling the directional indicator 148 with his or her fingers. Although variations of the device may include visual directional indicators 151 as shown in FIG. 5 to visually indicate the direction of the distal end of the injection tubing, the ability to identify the tactile protrusion 150 via touch alone allows the physician to focus his or her attention elsewhere.

In certain variations where the injection tubing 110 cannot rotate within the needle cannula 102, the directional indicator 148 and/or tactile protrusion 150 can be located on a hub 106 of the needle cannula 102. Accordingly, the directional indicator 148 and/or tactile protrusion 150 tracks rotation of the hub 106 and needle cannula 110 and therefore also track the orientation or direction of the curved portion 109 of the injection tubing 110. However, in alternate variations, the directional indicator 148 and/or tactile protrusion 150 or FIG. 3A can be located on the injection tubing (distal to the hub), extension line, or on plunger/sliding member 122 of the injection tubing 120. In such a variation, the injection tubing 120 is rotatable as well as axially advanceable relative to the hub 106 and needle cannula 102 so that the directional indicator 148 and/or tactile protrusion 150 tracks rotation of the orientation/direction of the curved portion 109 of the injection tubing 110. In most cases, rotation of the injection tubing 110 will occur after it is withdrawn into the needle cannula 102. As noted herein, the injection tubing 110 and/or sliding member 122 can rely on keys, indents, detents, etc. so that the sliding member is rotatable to less than 360 degrees or have tactile indications to identify rotation of the device.

Figure 4A:
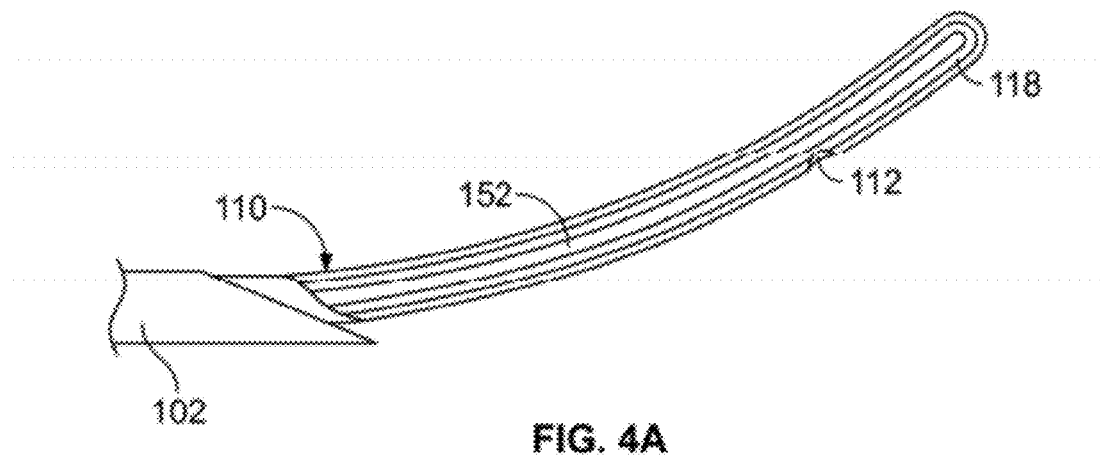
FIGS. 4A to 4C illustrate additional variations of injection tubing having one or more wires within an injection lumen.
Figure 4B:
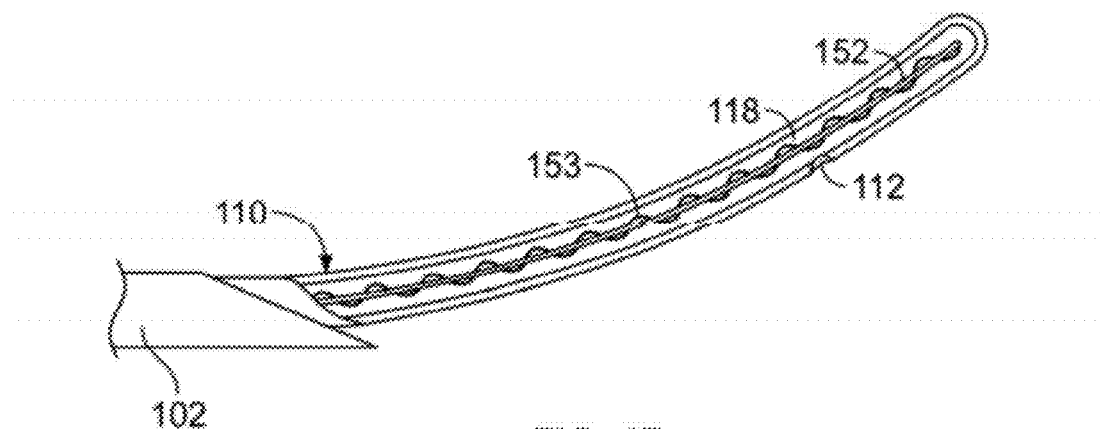
Figure 4C:
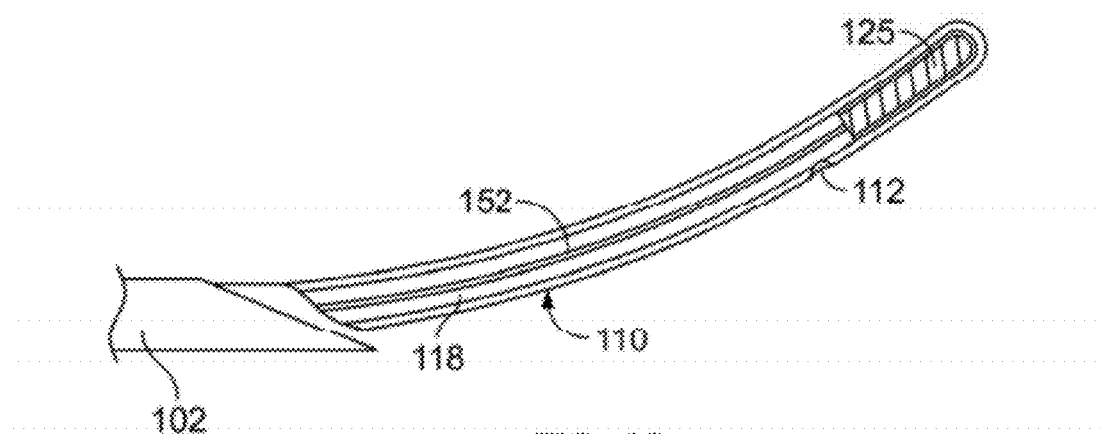

FIGS. 4A to 4C illustrate additional variations of injection tubing 110 for use with systems described herein. One common concern with spinal injection systems is that, during or after a procedure, a physician could shear the injection tubing 110 against the needle 102 and causes a piece of the device to remain within the body. Such debris could cause additional complications to the patient and/or require more invasive surgical intervention. To reduce the chances of shearing of the injection tubing 110, variations of the device can include, as shown in FIG. 4A, one or more reinforcement wires 152 extending through the injection tubing 110. Such wires can serve multiple purposes of providing a radiopaque target (where the wire can be a highly radiopaque material), a material that provides a shape to the elongate tubing 110 (e.g., a resilient alloy, set superelastic alloy or a shape memory alloy that assumes a shape upon reaching a certain temperature); and/or a combination of such materials. In any case, the wires should be sized to allow for sufficient fluid flow so that a fluid medium can be delivered from the port 112.

FIG. 4B illustrates another variation of an injection tubing 110 having a first and second wire 152 153 located in the fluid lumen. In this variation, one wire can provide additional flexibility or shape support to the injection tubing 110 while the second wire could provide added radiopacity. Although the illustration shows one wire helically wrapped about a second wire, both wires could be helically wrapped together. The helical wrapping can also create a helical channel for delivery of the fluid medium through the injection lumen 118. In additional variations, the variations shown in FIGS. 4A and 4B can further include a radiopaque marker coupled to the wires.

FIG. 4C illustrates another variation of an injection tubing 110 having a wire 152 located in the fluid lumen 118 coupled a radiopaque marker 125. In this variation, the wire 158 can provide the structural or imaging characteristics described above while also being a tether to the distal tip to prevent accidental shearing by the needle cannula 102.

Figure 6A:
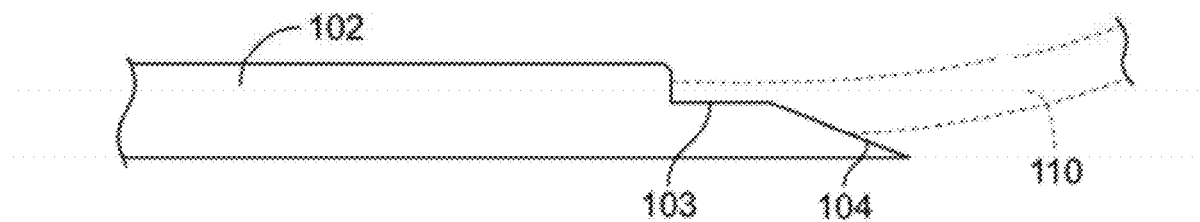
FIGS. 6A and 6B illustrate side and top views respectively of a variation of a needle cannula having a recess adjacent to the tip of the cannula to create additional clearance for the injection tubing to enter and exit the cannula.
Figure 6B:
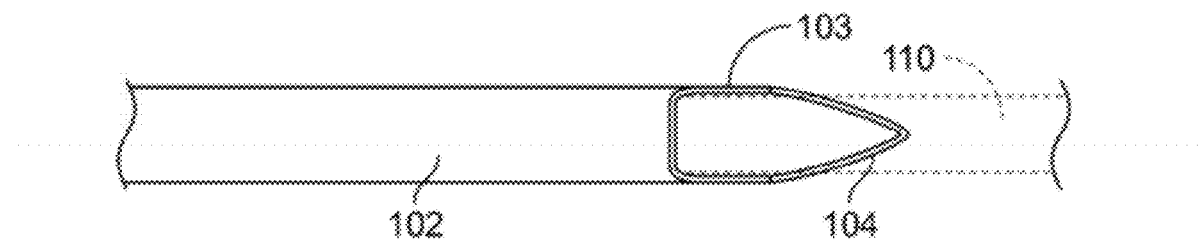

FIGS. 6A and 6B illustrate side and top views respectively of a variation of a needle cannula 102 having another safety feature for use with variations of the systems described herein. As noted above, the small size of the injection tubing creates a risk that the needle cannula 102 could shear the tip or end of the injection tubing 110 resulting in potentially dangerous debris within the body. To reduce the likelihood of shearing the injection tubing 110, a cannula needle 102 can include a recessed section 103 adjacent to a sharp tip 104. The recessed section 103 removes the heel of the tip 104 to create added clearance for the curved portion of the injection tubing 110 to enter and exit the cannula 102.

Figure 7A:
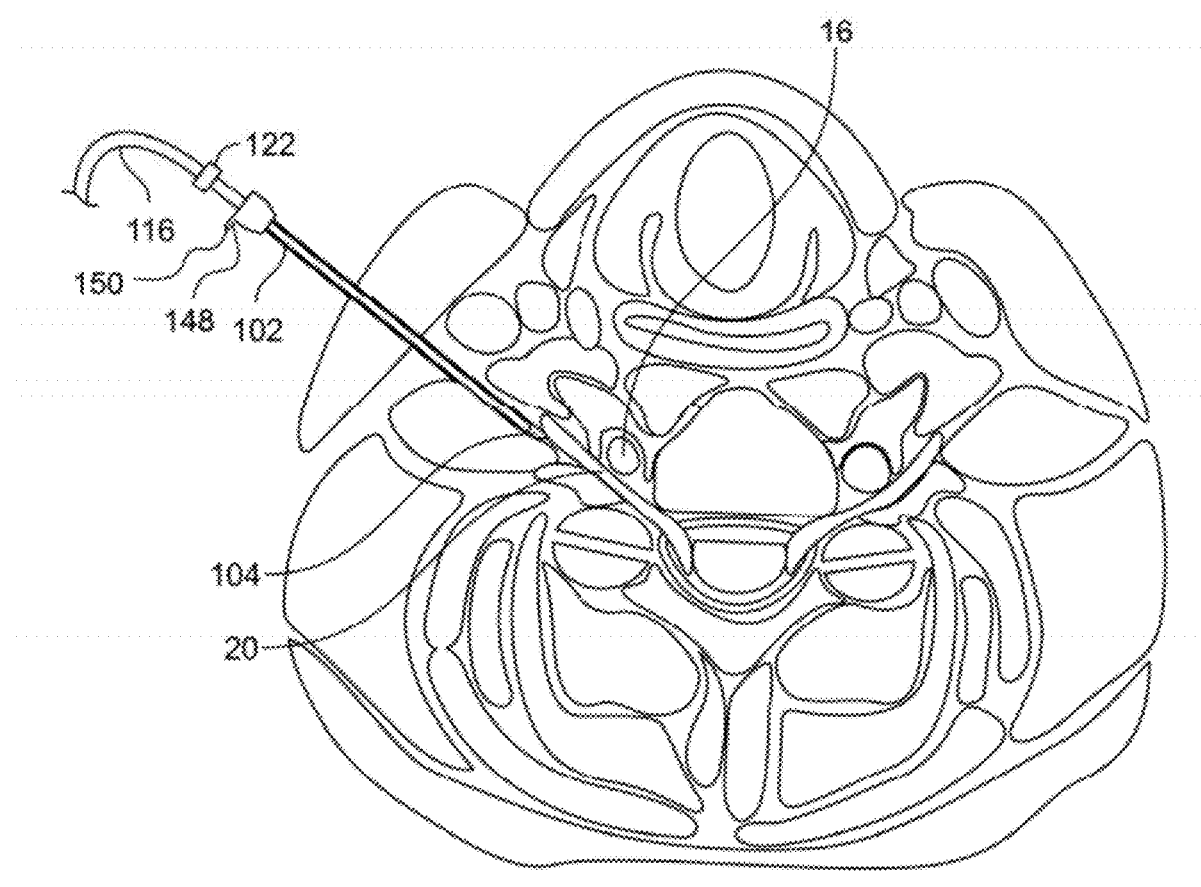
FIGS. 7A to 7B illustrate an example of placing and deploying the injection systems according to the devices and methods described herein.

FIG. 7A shows an example of placement of the injection system within the body. As illustrated, the needle is positioned in the patient under fluoroscopic guidance in the manner described in the conventional procedure, with the exception that the distal tip 104 of the cannula is positioned approximately 5 mm proximal to the intended target site (typically the epidural space or spinal foramen).

The epidural space is generally defined as the space outside the thecal sac and bounded ventrally by the posterior aspect of the vertebral body or the intervertebral disk, dorsally by the ligamentum flavum and facet capsule, and laterally to a line drawn in the coronal plane down the lateral third of the pedicle. As noted herein, one variation of the invention positions the needle cannula outside of the epidural space. However, the devices, systems and methods described herein can be placed anywhere within the body (either totally or partially within the epidural space or spaced a significant distance away.) In either case, the systems and devices described herein are intended to reduce or prevent accidental trauma to various structures in or near the vertebral body during an injection.

This position keeps the sharp tip 104 away from critical vasculature 16 and nerves 20. As shown, the plunger 122 is in a proximal or retracted position, which maintains the distal portion of the injection tube 110 within the cannula 102. The operator can confirm placement of the cannula 102 by injecting the contrast agent or dye in the manner described above or by simply observing the cannula 102 under fluoroscopy or x-ray. In addition, the physician can track orientation of the needle bevel or tip 104 using the directional indicator 148 and or tactile protrusion 150 (in those variations that include such a feature). The indicator 148 and/or protrusion 150 allow the physician to adjust the rotation of the cannula 102 prior to delivery of the Substance or prior to advancement of the injection tube from the needle cannula 102. As discussed herein, the directional indicator 148 and or tactile protrusion 150 can also be located on the plunger 122. In such a case, the indicator 148 and protrusion 150 only tracks the direction of the curved portion of the injection tubing 110.

The operator holds the hub 106 and/or the cannula 102 while advancing the device through the skin and soft tissue.

Once positioning of the cannula is properly determined, the portion of the cannula 102 or the hub 102 can be secured to the exterior skin or operating table in such a manner as to stabilize it from penetrating deeper or withdrawing from the patient, or moving laterally. A second method of stabilization may be an adhesive pad with an integrated clamp that adheres to the patients' skin and stabilizes the needle relative to the patients' skin.

Figure 7B:
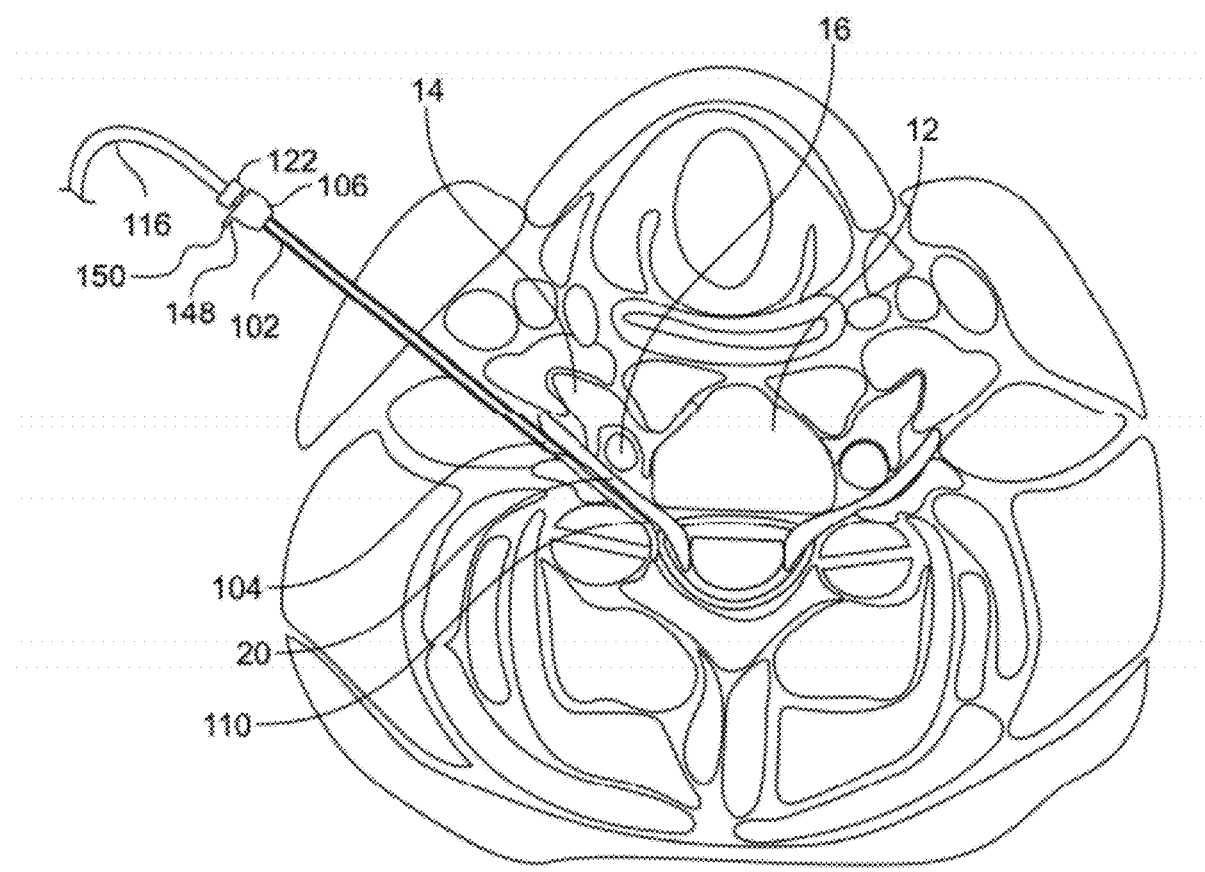

Once the distal tip 104 of the cannula 102 is in position and clamping or adhesive pads are applied the operator is ready for advancing the injection tube. As shown in FIG. 7B, the operator confirms the direction indicated by the directional indicator 148 and or tactile protrusion 150. Once the device is positioned as desired, the operator advances the plunger 122 causing advancement of the injection tube 110 to the target site (in one variation the system 100 allow advancement of the tip 120 of the injection tube 5 mm to the site). As discussed herein, variations of the device include an injection tube 110 having a slight radius or curve at a distal portion 114 that enables advancement of the distal portion 114 along a curved path that is biased toward the posterior aspect of the foramen. Again, the direction of the path is tracked by the directional indicator 148 and or tactile protrusion 150. This curved position keeps the injection tube 110 safely away from the vasculature and the nerve root which reside in the proximity of the injection site. Additionally, there is a reduced likelihood that the injection tube 110 will penetrate vessels if it engages the vessels during advancement due to the features of the injection tube 110. For example, one variation includes a flexible, curved, elastic catheter to significantly reduce the likelihood of injecting medication into a blood vessel. In such a case, the injection tube catheter is not sharp enough or rigid enough to perforate the wall of the blood vessel. As noted above, variations of the injection tube includes a blunt tip 120. In addition, variations of the device used in spinal applications shall be flexible.

The injection port 112 is located away from the distal tip 120 (in one example the injection port is spaced 2 mm away from the tip, but any spacing that places the injection port 112 on the distal portion of the device is contemplated.) This feature prevents inadvertent vascular uptake since it would be necessary to cannulate the distal portion of the injection tube within the blood vessel over a distance long enough to envelope the injection port as well. Furthermore, in those variations where the injection port is placed on an interior radius or aspect of the curved distal portion, fluid delivery occurs towards a portion of the vertebral body 12 rather than against a vessel or nerve.

Prior to delivery of the substances, the operator can also observe, under fluoroscope, the position of the distal portion 114 of the injection tube 110 and even the placement of the injection port 112 by observing the position of one or more radiopaque markers on the distal portion. As noted above, some variations include placing a radiopaque mark or indicator directly adjacent to the injection port thereby enabling the operator to see the exact position where the injection will occur.

After verifying the correct position of the injection tube and injection port, the operator continues in the same sequence as the conventional procedure described above. For example, the operator injects radio-opaque dye into the site to verify the tip of the injection tubing is in the correct location and that a blood vessel was not inadvertently breached as evidenced by the uptake of radio-opaque dye into the vessel. Next, an injection of a test dose of local anesthetic such as lidocaine is administered followed by a sixty second waiting period before a second lidocaine dose and or corticosteroid is injected. The lidocaine is injected first and patient observed to ensure that there has not been intravascular, especially intra-arterial uptake.

As noted herein, because all three syringes can be attached to the system 100, it is not necessary to exchange syringes between injection sequences. This feature not only improves operator convenience and reduces finger fatigue from the syringe exchange, but more importantly, it improves patient safety by reducing the likelihood of inadvertent cannula movement during syringe exchanges. In addition, placement of the syringes outside of the surgical field or away from the fluoroscope. Operator safety is further improved because the physician administering the injections may perform the injection of contrast media safely away from the injection site while using real time direct fluoroscopy. This reduces operator cumulative exposure to X-Ray radiation hazards.

After the injection sequence is completed, the cannula 102 can be removed from the injection site with or without the injection tube 110 retracted into the cannula 102.

The volume of fluid in the common fluid path of the catheter system (the volume of fluid that remains between the manifold and the injection port of the injection tube), is considered insignificant. In one variation of a system for cervical injection, this volume is approximately 0.02 ml whereas the typical injection volume of anesthetic is 0.5 ml (0.4% flush volume), and the injection volume or steroid is 2.0 ml (0.16% flush volume). Both of these flush volumes are within the "noise level" of operators' ability to administer a measured dose of injectants. Therefore, it is not necessary to flush the common fluid path between injections, (e.g. between radio-paque dye, anesthetic, and corticosteroid).

Although the examples discussed herein, primarily relate to injection systems suited for injections in the cervical region of the spine, the features of the system may be used for spinal treatments in the lumbar and thoracic regions as well.

Figure 8A:
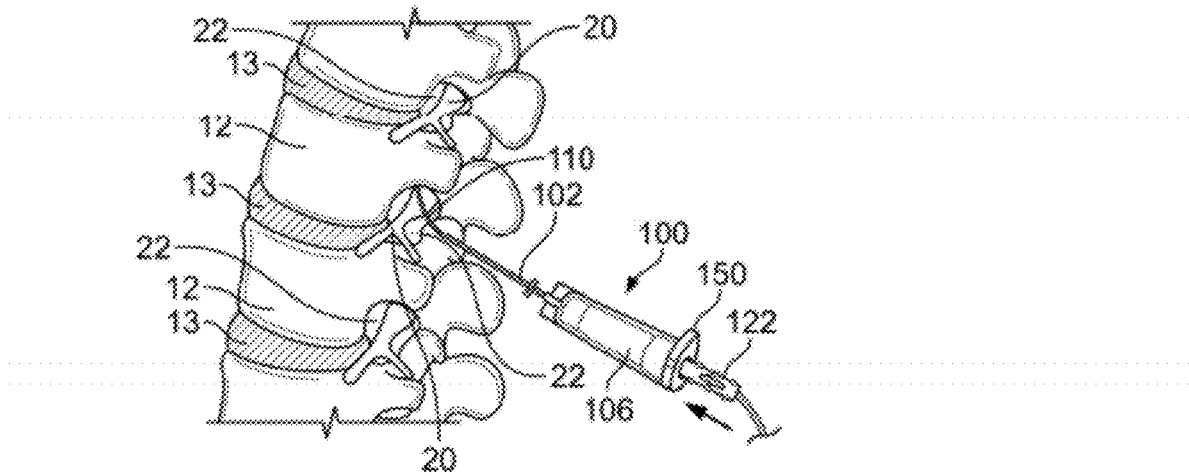
FIGS. 8A to 8C illustrate a variation of delivering injections in a lumbar region of the spine using the devices, systems, and methods disclosed herein.
Figure 8B:
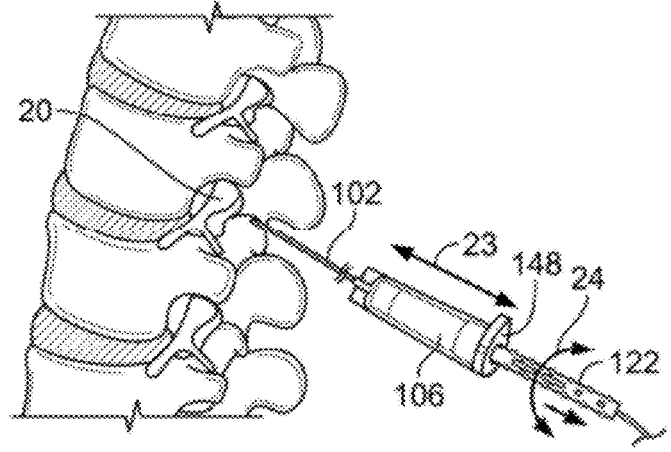
Figure 8C:
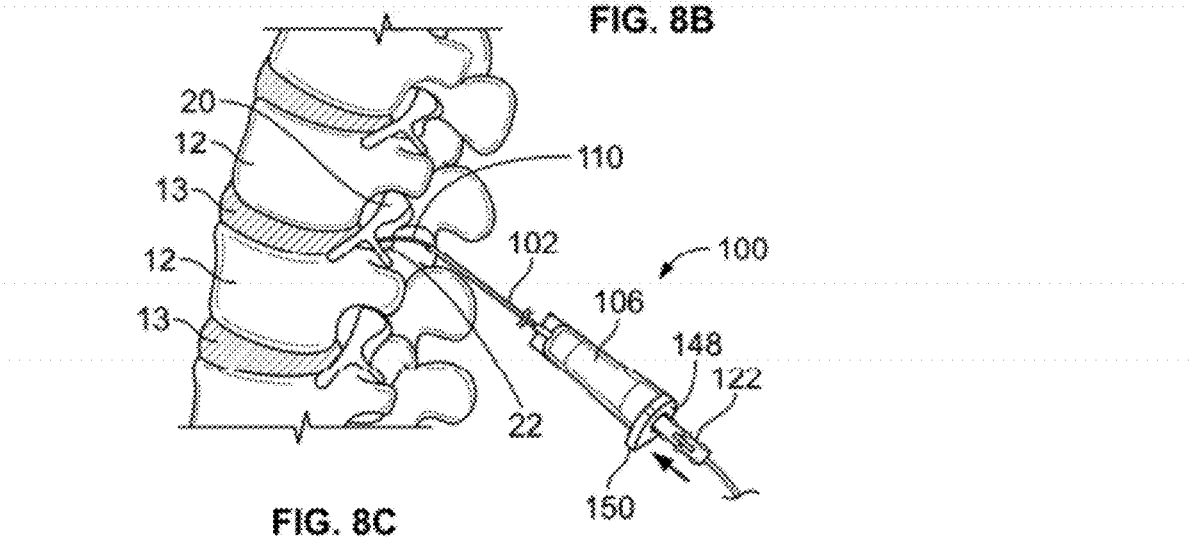
Figure 9A:
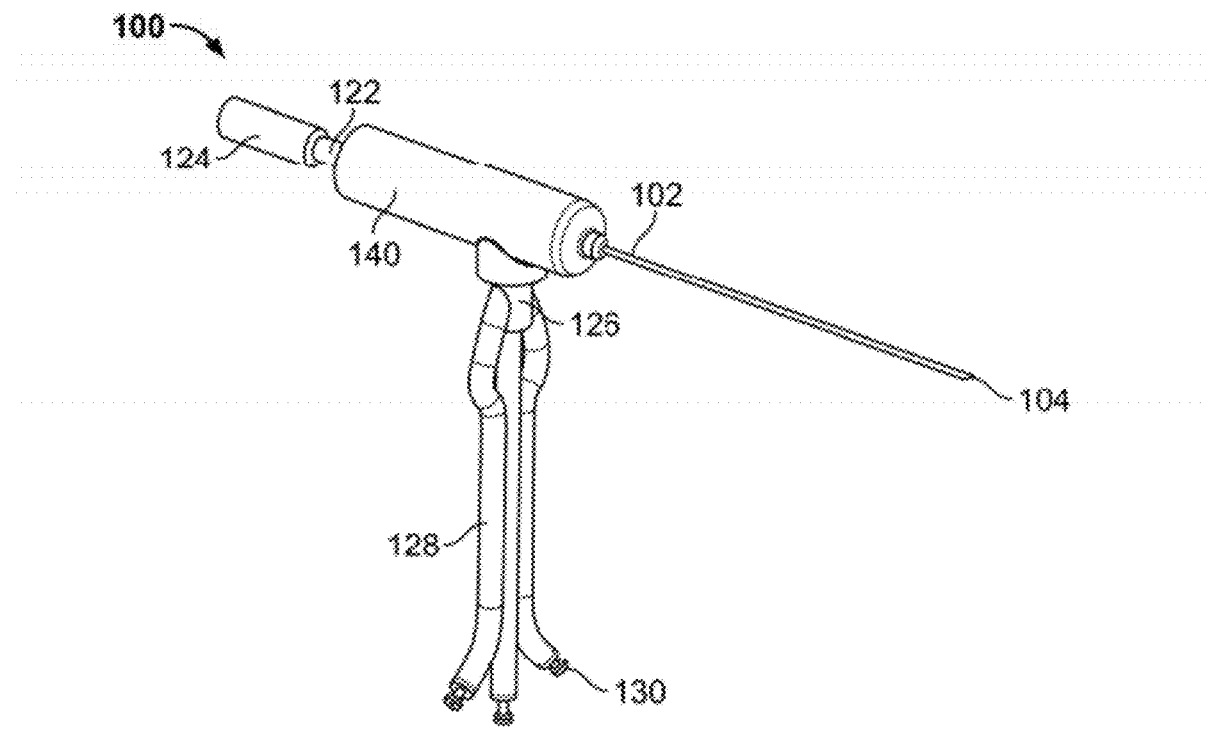
FIGS. 9A to 9D show additional variations of injection systems where a manifold is located on a body of the device.
Figure 9B:
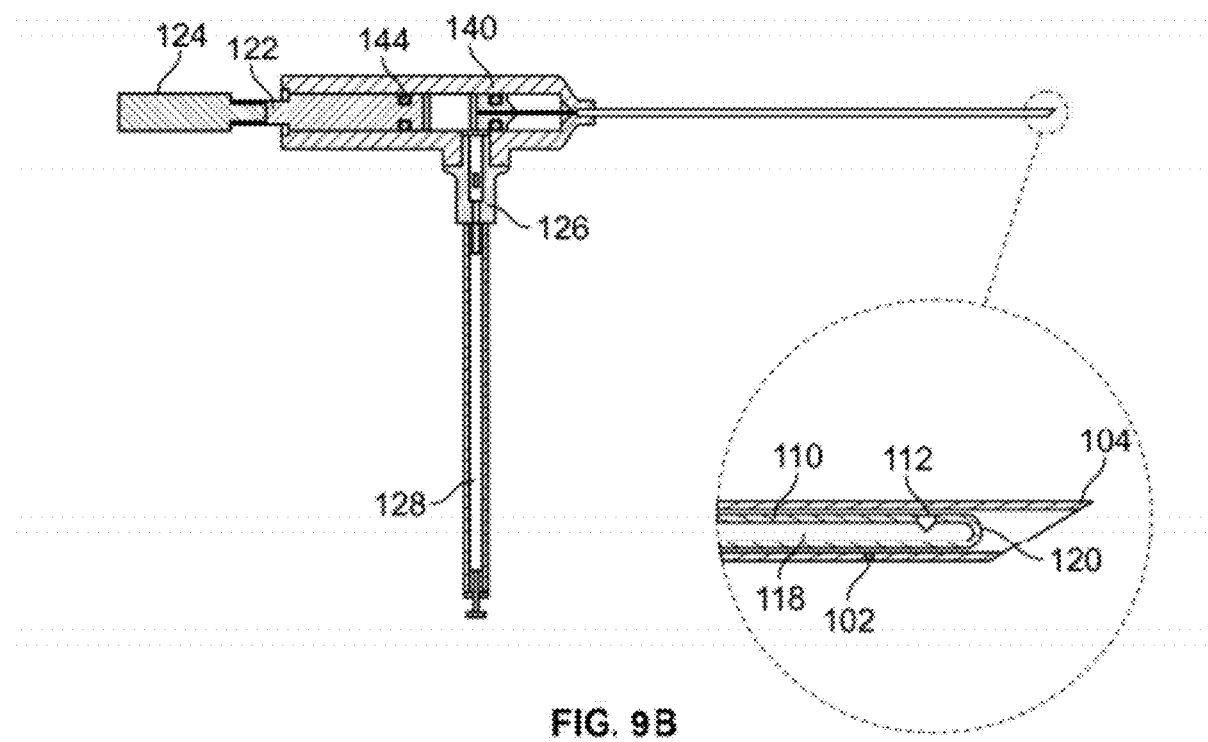
Figure 9C:
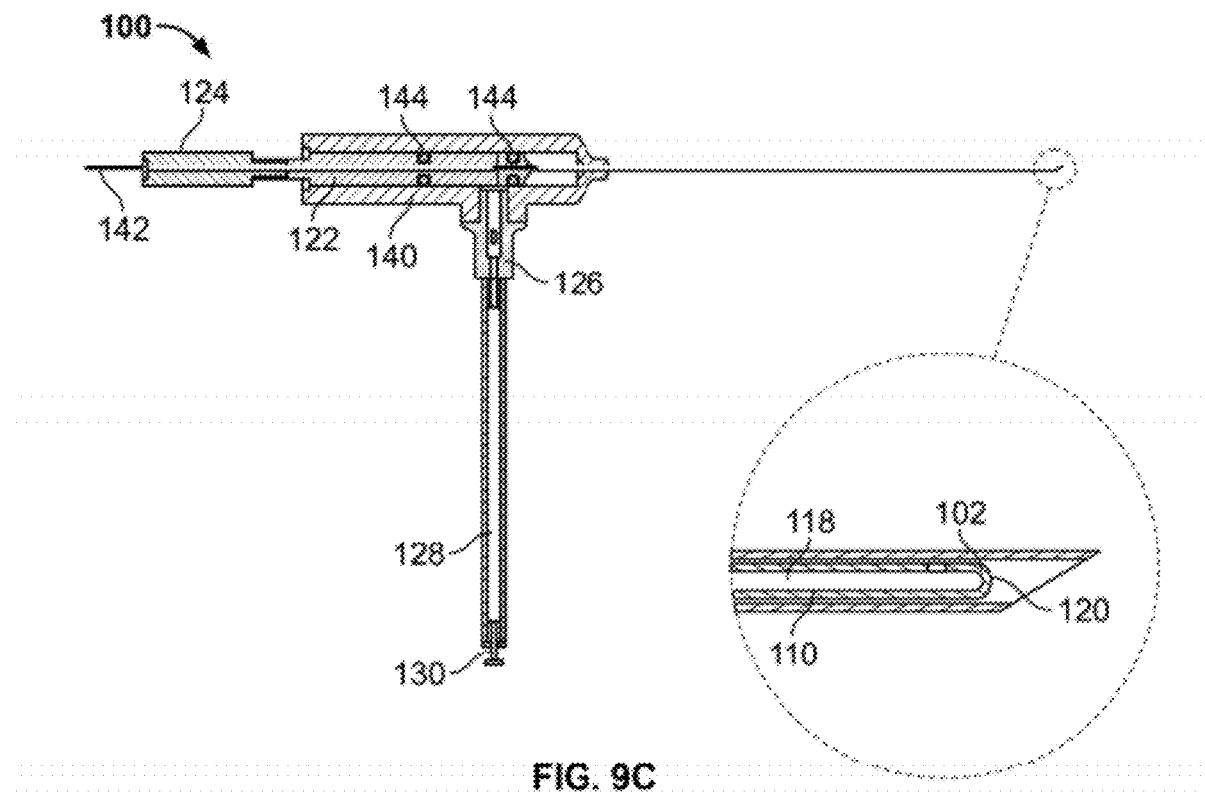
Figure 9D:
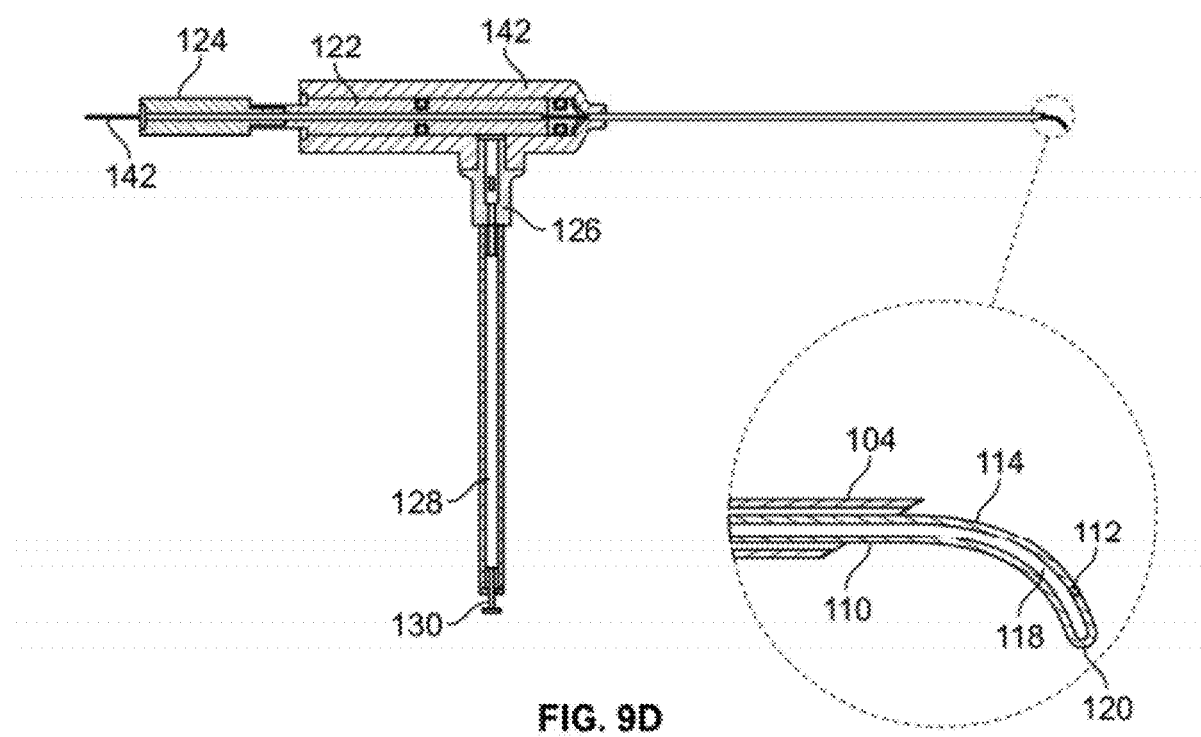

For example, FIGS. 8A to 8C illustrate a variation of the system 100 for use in delivering injections in a lumbar region of the spine. As with the other variations shown herein, the system 100 provides a physician with access to a region in or adjacent to a vertebral body 12 or vertebral disc 13. In the illustrated example, the physician can access a lateral recess 22 directly, thereby depositing medication at the true source of pathology (the irritated nerve 20.) Variations of the systems and devices described herein provide enables the physician to position the tip of the needle cannula 102 safely away from the exiting nerve root 20 prior to advancing an injection tubing 110 (typically a flexible, curved, elastic catheter) into the foramen and lateral recess 22 to inject any fluid medium (e.g., medication or other substances described herein) directly into the desired site. Either the needle can be spaced from the foramen and vertebral body (e.g., the needle does not enter the epidural space) or the needle can be advanced near to or within the vertebral body/foramen. As shown in FIG. 8A, the injection tubing 110 then traverses the foramen and advances in a curved path (as tracked by the orientation of the tactile member 150), thereby eliminating or dramatically reducing the incidence of nerve root contact and the associated sequelae as discussed above.

Another advantage of the present system allows a physician to enter a superior and inferior lateral recess of two adjacent spinal levels (as shown in FIGS. 8A and 8C). As a result, the dual access reduces total procedure time by treating two levels with a single needle and insertion versus the use of two needles to treat two levels. For example, to complete an injection sequence at a first level (as shown in FIG. 8A), the needle cannula 102 is outside a foramen of the verebral body 12 (in this case the L4-L5 foramen). The physician then passes the injection tubing 110 into the lateral recess 22 (e.g. at L4-L5) and completes an injection at the traversing nerve root (L4).

Next, the physician can remove the device 100 from the body, or optionally deliver a second injection without removing the device from the body. For example, as shown in FIG. 8B, the physician can retracts the injection tubing into the needle cannula 102 and rotate either the needle cannula 102 (e.g., via the needle hub 106) or rotate the injection tubing via the sliding member or plunger 122 to "re-aim" or "re-orient" the curved distal end of the injection tube by reorienting the device 100 either rotationally and/or axially as shown by arrows 23 and 24. One benefit of this system is that the needle can remain within the body of the patient rather than requiring reinsertion (i.e., the needle is repositioned without changing the needle entry point.) Again, at any point the physician can track rotation via the directional indicator 148. Typically, the physician will track the location of the injection tubing 110 prior to the initial advancement out of the needle cannula as well as prior to any subsequent advancement out of the needle (e.g., after repositioning of the needle).

FIG. 8C shows the system 100 after either the plunger/sliding member 122, hub 106, or needle cannula 102 (depending on the configuration of the device) is rotated. As noted, the directional indicator 148 indicates the movement of the injection tubing 110 in an inferior lateral recess 22. In the illustrated example, the injection tubing 110 advances it into the descending lateral recess adjacent to the L5 nerve root to deliver the fluid medium.

FIGS. 8A-8D illustrate another variation of a system 100 according to the concepts of the present disclosure. In this variation, the manifold is directly coupled to a device body 142.

As shown in FIG. 8A, the components of this variation include a cannula needle 102, a catheter or injection tube (not shown in FIG. 8A) coupled to a plunger 122, a device body 140, a manifold 126, extension lines or tubes 128, luer connectors 130. As noted above, in additional variations, an internal stop surface located within the hub 106 can replace the plunger 122.

FIG. 8B illustrates a cross sectional view of the system of 8A. As shown, the body 140 of the injection system 100 may be cylindrical in shape for ease of manipulation. The manifold 126 can extend from the side of the body 13 to permit the flow of injectables (as discussed above) from the extension lines 128 into the injection tube 112. The extension lines 128 may be a single multi-lumen cross-section or may comprise the plurality of individual tubes shown. As discussed herein, the manifold 126 combines the flow of injectables from a plurality of sources (e.g., syringes) into a single injection lumen 118 for delivery through the injection port 112. Naturally, there will be sealing members 144 (such as o-rings) to prevent leakage of fluids from the interior of the body 140.

In this variation, the plunger 122 can have any shape, but shall have a portion slidably affixed within the interior of the device body 130. An upper portion of the plunger 122 extends out of the device body 130 allowing for an operator to actuate or slide the injection tubing in and out of the cannula 102. The plunger 122 is affixed to the injection tubing 110 on its lower end with a lumen extending from the catheter to the sealed cavity within the lumen of the body cylinder to allow the injectable fluids to flow from the manifold into the catheter. The upper portion of the plunger 122 that extends out of top of the body 140 allows the operator to grip the plunger between their forefinger and thumb, thus providing a tactile "feel" of the resistance as the catheter is advanced to the injection site. However, as noted above, the tipper portion of the plunger 122 can simply comprise shrink tubing that covers the plunger and extends over an inch or so of the injection tubing 110 to act as a stress relief. Similar stress relief structure can also be placed over the lip of the manifold to provide stress relieve the catheter on that end as well. Injectants, injectable fluids, and so forth are defined as any medication or diagnostic fluid the physician may choose to administer with the system.

In many variations of the device, the plunger has a limited stroke. This limited stroke allows for a known and finite advancement of the distal portion 114 of the injection tube 110 out of the cannula 102. In the variation shown, the plunger 122 has a stop on an exterior surface in the form of a raised surface 124. Alternatively, or in combination, a stop surface can be located on the injection tube, or even on the plunger portion that is interior to the hub 106. Naturally, any number of configurations is contemplated.

A flexible catheter or injection tube 110 resides within the cannula needle 102 and has a rounded or blunted tip 120 with an injection port or orifice 112 on the side of the catheter 110 near the distal portion 114. As noted above, catheter tubing of the present devices can be made from a flexible material those known in medical device applications and may have shaped memory characteristics that allow it to curve slightly around or deflect away from structures such as blood vessels, nerves, or bone to optimally position the orifice for the injections. The shape memory characteristics may come from the plastic properties of the catheter, an elastic wire that is extruded within the wall of the catheter, or an elastic stylus that temporarily resides in the lumen of the catheter.

Again, the injection tubing 110 includes an injection port 112 located on the side of the catheter tubing 110 to further reduce the likelihood of accidental injections into an artery.

Any of the variations discussed herein may include a clamp-stabilizer as an accessory device that holds the system stable relative to the neck. One embodiment of the clamp-stabilizer includes an adhesive pad that attaches to the body of the patient at the point of insertion. When the needle is in place, the clamp is activated to hold the needle stable relative to the patient.

One embodiment of the clamp-stabilizer includes a structure that attaches to a datum on the bed or bench where the patient is lying. The needle is positioned at the operative site and the clamp is activated to hold the needle steady as long as the patient does not move relative to the datum.

The flow path of the injectable fluids starts in the syringes attached to the connector 130. The tubing may be multi-lumen tubing or individual tubes. The fluid flows from the syringes through their respective individual lumens in the tubing and into the manifold on the side of the device body. The fluids then flow into interior cavity of the device body, into the plunger body, through the catheter and out the injection port on the side of the catheter near its distal end. An alternate variation includes a piece of tubing that connects the manifold directly to the proximal end of the catheter tubing thereby bypassing the interior of the device body.

As noted above and as shown 8C and 8D the system 100 may optionally include a stylus 142. The stylus 142 is can be incorporated into the injection tube 110 to aid in steering a tip of the injection tube 110 to a desired region. In an alternate variation, the system 100 includes a stylus that extends from inside the distal tip of the catheter tubing through the lumen of the catheter, through the body of the cylinder and exits the device through a membrane seal on the proximal surface of the plunger. The stylus is used by the operator to push the catheter out of the distal tip of the primary needle and into the injection site. The stylus could optionally have a curvature that translates its' curvature to the catheter to help steer the tip of the catheter along a curved path and into a position that is not accessible by a straight, rigid needle.

When the catheter tube is in position at the injection site, the stylus would be removed from the catheter to allow the injectants to flow through the catheter. The stylus may be supplied in a variety of curvatures to allow the operator to select the appropriate curvature to steer the catheter into position based on variations in anatomy or various injection modalities. Alternatively, the stylus may be constructed of a malleable material that allows the operator to shape the stylus to a custom curvature.

An alternate device embodiment would include a balloon on the tip of the catheter. The balloon would be inflated via a lumen in the catheter and would be used to anchor the catheter in place, dissect tissue, or steer the catheter by positioning the balloon on one side of the catheter such that it pushes the orifice of the catheter toward a particular injection site.

Before the present devices and method of treatment are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both or those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an aerosol" includes a plurality of such aerosols and reference to "the drug" includes reference to one or more drugs and equivalents thereof known to those skilled in the art, and so forth.

The publications discussed herein are provided solely For their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

What is claimed is:

1. A method of delivering one or more substances at an injection site near a vertebral body in a patient, the method comprising:
    providing an injection system including a needle cannula having a needle lumen extending therethrough and an injection tubing having a curved shape at a distal portion, where the injection tube is slidably located in the needle lumen to move between a retracted position and a deployed position, where in the retracted position the injection tubing remains within the needle lumen and in the deployed position the injection tubing extends out of a far end of the needle cannula such that the curved shape causes an end of the injection tubing to move away from an axis of the needle cannula, where an rotational indicator on the needle cannula correlates to the direction of movement of the end of the injection tubing;
    inserting a tip of the needle cannula into the patient so that the tip is positioned adjacent to the vertebral body;
    advancing the distal end of the injection tube around a feature of the vertebral body into a vertebral foramen by advancing the injection tube within the needle cannula such that the distal portion exits the needle cannula and assumes the curved shape to advance into a first lateral recess within the vertebral body;
    delivering at least a first substance at the first lateral recess;
    retracting the injection tube within the needle cannula without withdrawing the cannula from the body;
    rotating the needle cannula using the rotational indicator to rotationally position the needle cannula; and
    advancing the injection tube within the needle cannula such that the distal portion exits the needle cannula and assumes the curved shape to advance into a second lateral recess within the vertebral body, where the second lateral recess is adjacent to the first lateral recess.

2. The method of claim 1, where retracting the injection tube within the needle cannula without withdrawing the cannula from the body comprises retracting the injection tube then repositioning the needle cannula without removing the needle cannula from the body.

3. The method of claim 1, where using the rotational indicator to rotationally position the needle cannula comprising feeling a tactile feature on the rotational indicator to align the needle cannula with a desired orientation.

4. The method of claim 1, further comprising delivering at least the first or a second substance at the second lateral recess.

5. The method of claim 1, where advancing the tip of the needle cannula into the patient so that the tip is positioned adjacent to the vertebral body comprises positioning the tip in an epidural space.

6. The method of claim 1, where advancing the tip of the needle cannula into the patient comprises advancing the tip of the needle cannula through a vertebral foramen.

7. The method of claim 1, the first substance is selected from a group consisting of a radiopaque substance, an anesthetic, and an anti-inflammatory substance.

8. The method of claim 1, where the injection tubing is coupled to a plunger member having a limited range of movement within the needle cannula, where advancing the tip of the distal end of the injection tubing comprises advancing the plunger member within the needle cannula.

9. A method of delivering injections to multiple lumbar sites with a single needle insertion, the method comprising:

providing an injection system including a needle cannula having a needle lumen extending therethrough and an injection tubing having a curved shape at a distal portion, where the injection tube is slidably located in the needle lumen to move between a retracted position and a deployed position, where in the retracted position the injection tubing remains within the within the needle lumen and in the deployed position the injection tubing extends out of a far end of the needle cannula such that the curved shape causes an end of the injection tubing to move away from an axis of the needle cannula, where a rotational indicator on the needle cannula correlates to the direction of movement of the end of the injection tubing;

inserting a tip of the needle cannula into the patient so that the tip is positioned adjacent to the vertebral body;

advancing the distal end of the injection tube around a feature of the vertebral body into or adjacent to a vertebral foramen by advancing the injection tube within the needle cannula such that the distal portion exits needle cannula tube and assumes the curved shape to advance into a first lateral recess within the vertebral body;

retracting the injection tube within the needle cannula without withdrawing the cannula from the body;

rotating the injection tubing using the rotational indicator to rotationally position the needle cannula; and advancing the injection tube within the needle cannula such that the distal portion exits the needle cannula and assumes the curved shape to advance into a second lateral recess within the vertebral body, where the second lateral recess is directionally opposite to the first lateral recess.

10. The method of claim 9, where retracting the injection tube within the needle cannula without withdrawing the cannula from the body comprises retracting the injection tube then repositioning the needle cannula without removing the needle cannula from the body.

11. The method of claim 9, where using the rotational indicator to rotationally position the needle cannula comprising feeling a tactile feature on the rotational indicator to align the needle cannula with a desired orientation.

12. The method of claim 9, further comprising delivering at least the first or a second substance at the second lateral recess.

13. The method of claim 9, where advancing the tip of the needle cannula into the patient so that the tip is positioned adjacent to the vertebral body comprises positioning the tip in an epidural space.

14. The method of claim 9, where advancing the tip of the needle cannula into the patient comprises advancing the tip of the needle cannula through a vertebral foramen.

15. The method of claim 9, the first substance is selected from a group consisting of a radiopaque substance, an anesthetic, and an anti-inflammatory substance.

16. The method of claim 9, where the injection tubing is coupled to a plunger member having a limited range of movement within the needle cannula, where advancing the tip of the distal end of the injection tubing comprises advancing the plunger member within the needle cannula.

* * * * *